US007495152B2

(12) United States Patent
James et al.

(10) Patent No.: US 7,495,152 B2
(45) Date of Patent: Feb. 24, 2009

(54) IDENTIFICATION AND CHARACTERIZATION OF A NOVEL ALPHA-AMYLASE FROM MAIZE ENDOSPERM

(75) Inventors: Martha G. James, Des Moines, IA (US); Alan M. Myers, Ames, IA (US); Christophe Colleoni, Arques (FR); Kevin D. Stokes, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 11/891,589

(22) Filed: Aug. 10, 2007

(65) Prior Publication Data

US 2008/0134363 A1 Jun. 5, 2008

Related U.S. Application Data

(62) Division of application No. 10/952,551, filed on Sep. 27, 2004, now Pat. No. 7,270,988.

(60) Provisional application No. 60/505,995, filed on Sep. 25, 2003.

(51) Int. Cl.
*A01H 5/00* (2006.01)
*C12N 9/32* (2006.01)
*C12N 15/00* (2006.01)
*C12N 1/20* (2006.01)
*C12P 21/06* (2006.01)
*C07H 21/04* (2006.01)

(52) U.S. Cl. .................. 800/298; 435/204; 435/69.1; 435/252.3; 435/320.1; 536/23.2

(58) Field of Classification Search .................. None
See application file for complete search history.

(56) References Cited

U.S. PATENT DOCUMENTS

| 7,270,988 B2 * | 9/2007 | James et al. ............... 435/204 |
| 2004/0034888 A1 | 2/2004 | Liu et al. ................... 800/289 |
| 2004/0214272 A1 | 10/2004 | La Rosa et al. ........... 435/69.1 |

FOREIGN PATENT DOCUMENTS

| WO | WO03027141 A1 * | 3/2003 |
| WO | WO 03/027141 A1 | 4/2003 |

OTHER PUBLICATIONS

Beck et al., "Biosynthesis and Degradation of Starch in Higher Plants" Annu. Rev. Plant Physiol. Plant Mol. Biol. (1989) 40: pp. 95-117.
French, D., "Organization of Starch Granules" Starch, 2nd Edition (1984) pp. 183-247.
Gallant et al., "Microscopy of Starch: Evidence of a New Level of Granule Organization" Carbohydrate Polymers 32 (1997) pp. 177-191.
Guzmán-Maldonado et al. "Amylolytic Enzymes and Products Derived from Starch: A Review" Critical Reviews in Food Science and Nutrition, 35(5) pp. 373-403.
Hodges et al., Biosynthesis of phytoglycogen in maize endosperm. The branching enzyme. Biochimica et Biophysica Acta., 185: 70-79, 1969.
Huala et al., "The Arabidopsis Information Resource (TAIR): A Comprehensive Database and Web-based Information Retrieval, Analysis, and Visualization System for a Model Plant" Nuceic Acids Research, 2001, vol. 29, No. 1, pp. 102-105.
Imberty et al., "Recent Advances in Knowledge of Starch Structure" , Starch, vol. 43, No. 10 (1991) pp. 375-384.
Jespersen et al., "Starch—and Glycogen-Debranching and Branching Enzymes: Prediction of Structural Featuers of the Catalytic $(\beta/\alpha)_8$-Barrel Domain and Evolutionary Relationship to Other Amylolytic Enzymes" Journal of Protein Chemistry. vol. 12 No. 6 (1993) pp. 791-805.
Kennedy et al., "Enzymic Starch Utilization and Genetic Engineering" (1988) pp. 184-189.
MacGregor, E. Ann, "Structure and Activity of Some Starch-metabolising Enzymes" Enzymes for Carbohydrate Engineering (1996) pp. 109-124.
Martin et al., "Starch Biosynthesis" The Plant Cell, vol. 7, pp. 971-985 Jul. 1995 © 1995 American Society of Plant Physiologists.
Myers et al., "Recent Progress Toward Understanding Biosynthesis of the Amylopectin Crystal [1]" Plant Physiology, Apr. 2000, vol. 122, pp. 989-997.
Ritte et al., "Reversible Binding of the Starch-related R1 Protein to the Surface of Transitory Starch Granules" The Plant Journal (2000) 21(4), pp. 387-391.
Robyt, John F., "Essentials of Carbohydrate Chemistry" Chapter 7 pp. 228-233, 1998.
Søgaard et al., "α-Amylases: Structure and Function" Carbohydrate Polymers 21 (1993) pp. 137-146.
Whistler et al, "Starch -Chemistry and Technology" 2nd Edition, Chapter 4 by Robyt (1984) pp. 87-123.
Zeeman et al., "A Mutant of *Arabidopsis* Lacking a Cloroplastic Isoamylase Accumulates Both Starch and Phytoglycogen" The Plant Cell, vol. 10, pp. 1699-1711, Oct. 1998.
Zeeman et al., "A Strach-Accumulating Mutant of *Arabidopsis thaliana* Deficient in a Cloroplastic Starch-Hydrolysing Enzyme" The Plant Journal (1998) 15(3), pp. 357-365.

* cited by examiner

*Primary Examiner*—Rebecca E. Prouty
*Assistant Examiner*—Ganapathirama Raghu
(74) *Attorney, Agent, or Firm*—Weingarten, Schurgin, Gagnebin & Lebovici LLP

(57) ABSTRACT

SHE, a Starch Hydrolytic Enzyme active in maize endosperm (*Zea mays*), and the cDNA sequence encoding SHE are disclosed. The specificity of native, purified SHE is similar, in general terms, to previously known alpha-amylases. However, the activity of SHE toward amylopectin results in hydrolysis products that are distinctly different from those of other alpha-amylases. SHE, and its homologous equivalents in other plants such as rice, *Arabidopsis*, apple and potato, can be used in starch processing for generating different, e.g., larger sized, alpha-limit dextrins for industrial use, as compared to those generated by previously known alpha-amylases or other starch hydrolytic enzymes. In addition, modification of the expression of this enzyme in transgenic maize plants or in other transgenic organisms (including bacteria, yeast, and other plant species) can be useful for the generation of novel starch forms or altered starch metabolism.

14 Claims, 13 Drawing Sheets

Analysis of the hydrolysis products of purified SHE incubated with amylopectin

Analysis of the hydrolysis products of purified SHE incubated with amylopectin

MALTI-TOF analysis of 94kD protein

Data Set 1 Results

MS-Fit search selects 8625 entries (results displayed for top 50 matches).

Results Summary

| | MOWSE Score | #/196(%) Masses Matched | % Cov | % TIC | Mean ERR ppm | Data Tol ppm | MS-Digest Index # | Protein MW (Da)/pI | Accession # | Species | Protein Name |
|---|---|---|---|---|---|---|---|---|---|---|---|
| 1 | 1.063e+05 | 11 (5) | 15.0 | 5.6 | 0.608 | 33.5 | 1003992 | 101642/5.9 | 21104772 | ORYZA SATIVA (JAPONICA CULTIVAR-GROUP) | (putative alpha-amylase) |
| 2 | 3.131e+04 | 10 (5) | 15.0 | 5.1 | 9.53 | 29.9 | 359695 | 108668/6.1 | 6322548 | M UNREADABLE | gi|6322548|ref|NP_012622.1| baculoviral IAP repeat-containing protein; Bir1p [Saccharomyces cerevisiae] |
| 3 | 2.436e+04 | 9 (4) | 10.0 | 4.6 | 0.342 | 25.4 | 369468 | 119644/5.0 | 15642836 | M UNREADABLE | gi|15642836|ref|NP_227877.1| endo-1,4-beta-xylanase A [Thermotoga maritima] |

*FIG. 8*

```
            M   X   K   S   S   L   S   L   S   R   S   I   F   L   X   R   F   G   S   L
   1   ATGNANAAATCTTCTCTCTCTCTCCCGCTCTATTTTTCTCATNCGCTTCGGCTCCCTC
            T   H   S   H   A   H   T   R   X   X   H   T   P   A   L   S   E   R   E   R
  61   ACACACTCACACGCACACACNAGAGNNNCGCACACACCCGCTCTCTCAGAGAGAGAGA
            E   R   A   S   H   V   G   G   E   L   L   H   S   C   Y   P   G   A   A   E
 121   GAGAGAGCTAGCCATGTCGGTGGGGAGTTGTTGCATTCGTGCTATCCCGGGGCCGCGGAG
            S   A   V   A   G   T   D   E   D   A   G   A   A   F   S   E   T   F   P   L
 181   AGCGCGGTGGCTGGCACTGACGAGGACGCTGGAGCGGCGTTCTCCGAGACGTTCCCCCTG
            R   R   C   Q   A   V   E   G   K   A   W   V   R   V   D   A   E   P   D   S
 241   CGCCGATGCCAAGCTGTGGAAGGGAAGGCGTGGGTGAGGGTGGACGCAGAGCCGGACTCC
            E   G   K   C   K   V   V   V   G   C   N   V   A   G   K   W   V   L   H   W
 301   GAAGGCAAGTGCAAGGTCGTTGTTGGGTGTAATGTGGCGGGGAAGTGGGTACTGCACTGG
            G   V   S   Y   D   D   E   H   G   R   E   W   D   Q   P   P   S   E   M   R
 361   GGTGTCTCGTACGATGATGAACATGGAAGAGAATGGGATCAGCCTCCTTCAGAAATGAGA
            P   P   G   S   V   A   I   K   D   Y   A   I   E   T   P   L   E   I   L   P
 421   CCACCTGGTTCAGTTGCAATCAAGGACTATGCAATTGAAACACCATTGGAGATTTTGCCC
            N   S   E   G   Q   P   L   Y   E   M   Q   I   K   F   D   K   D   I   P   I
 481   AATTCAGAAGGACAGCCCCTTTATGAAATGCAAATCAAATTTGATAAAGACATTCCAATC
            A   A   V   N   F   V   L   K   E   E   E   T   G   A   W   F   Q   H   K   G
 541   GCCGCTGTCAACTTTGTTCTAAAGGAAGAGGAAACAGGTGCATGGTTTCAGCATAAGGGC
            R   D   F   R   I   P   L   N   G   S   F   N   D   G   G   K   Q   D   I   D
 601   AGGGATTTCAGAATACCCTTAAATGGATCCTTCAATGATGGCGGAAAACAAGATATTGAT
            I   W   P   G   D   L   G   H   V   L   K   K   S   E   G   S   S   S   Q   P
 661   ATCTGGCCAGGAGATTTGGGGCATGTATTGAAGAAATCTGAAGGCTCTAGTTCTCAGCCA
            Q   N   T   S   P   E   D   T   G   L   S   G   K   H   I   S   G   F   Y   E
 721   CAAAACACTTCACCTGAGGATACAGGTTTGAGTGGCAAACATATATCAGGGTTCTATGAG
            E   Y   P   I   L   K   S   E   Y   V   Q   N   L   V   T   V   T   V   R   R
 781   GAATACCCCATCCTTAAATCAGAGTATGTTCAGAATCTTGTTACTGTCACTGTGAGGAGA
            D   I   E   A   H   K   R   L   V   E   F   D   T   D   I   P   G   E   V   I
 841   GACATTGAAGCGCATAAAAGACTTGTGGAATTTGACACTGATATTCCTGGAGAAGTTATC
            I   H   W   G   V   C   R   D   N   T   M   T   W   E   I   P   P   E   P   H
 901   ATTCATTGGGGAGTTTGCAGAGACAATACTATGACATGGGAGATCCCACCAGAACCACAT
            P   P   K   T   K   I   F   R   H   K   A   L   Q   T   L   L   Q   Q   K   A
 961   CCACCAAAAACGAAAATATTCCGACACAAAGCTCTTCAAACTTTGCTGCAGCAAAAAGCT
            D   G   A   G   N   S   I   S   F   S   L   D   A   E   Y   S   C   L   F   F
1021   GATGGAGCAGGAAACTCAATTTCATTCTCACTTGATGCAGAGTATTCTTGTCTGTTTTTT
            V   L   K   L   D   E   Y   T   W   L   R   N   L   E   N   G   S   D   F   Y
1081   GTGCTCAAACTTGACGAGTATACTTGGTTGAGAAATCTTGAGAATGGATCTGATTTCTAT
            V   P   L   T   R   V   G   Q   Y   G   S   T   Q   D   P   D   K   A   E   A
1141   GTGCCACTTACAAGAGTGGGGCAGTATGGCAGCACTCAGGATCCTGACAAGGCTGAGGCA
            Q   K   I   E   D   K   S   S   Q   A   D   G   L   I   S   D   I   R   N   L
1201   CAGAAAATAGAGGATAAGTCTTCACAGGCTGATGGCTTAATCAGTGATATAAGAAATCTG
            V   V   G   L   S   S   R   R   G   Q   K   A   K   N   K   V   L   Q   E   D
1261   GTGGTTGGCCTATCGTCTAGAAGAGGTCAGAAAGCTAAGAATAAAGTTCTTCAAGAGGAC
            I   L   Q   E   I   E   R   L   A   A   E   A   Y   S   I   F   R   S   P   T
1321   ATCCTACAAGAAATCGAAAGACTTGCAGCAGAAGCTTATAGCATTTTCAGGAGCCCCACT
            I   D   S   V   D   E   S   V   Q   L   D   D   T   L   S   A   K   P   A   C
1381   ATTGATTCCGTAGATGAATCTGTACAGCTCGATGACACATTAAGCGCAAAGCCAGCATGT
            S   G   T   G   S   G   F   E   I   L   C   Q   G   F   N   W   E   S   H   K
1441   TCTGGCACTGGATCTGGTTTTGAGATATTGTGCCAAGGATTTAACTGGGAATCTCATAAA
            S   G   K   W   Y   V   E   L   G   T   K   A   K   E   L   S   S   L   G   F
1501   TCAGGGAAATGGTATGTTGAGCTTGGCACAAAGGCCAAGGAGTTGTCGTCCTTGGGTTTC
```

*FIG. 9A*

```
         T  I  V  W  S  P  P  P  T  D  S  V  S  P  E  G  Y  M  P  R
1561  ACCATTGTCTGGTCACCACCACCAACTGATTCTGTGTCACCTGAAGGATACATGCCAAGG
         D  L  Y  N  L  N  S  R  Y  G  S  M  D  E  L  K  E  L  V  K
1621  GATCTATATAATCTAAACTCACGATATGGGTCCATGGATGAGCTGAAGGAACTTGTGAAG
         I  F  H  E  A  G  I  K  V  L  G  D  A  V  L  N  H  R  C  A
1681  ATTTTCCATGAAGCTGGTATCAAGGTTCTTGGCGACGCTGTTCTAAATCATAGGTGTGCT
         Q  F  Q  N  N  N  G  V  W  N  I  F  G  G  R  M  N  W  D  D
1741  CAGTTTCAGAACAACAATGGTGTCTGGAATATATTTGGTGGTCGTATGAACTGGGATGAT
         R  A  V  V  A  D  D  P  H  F  Q  G  R  G  N  K  S  S  G  D
1801  CGAGCAGTTGTTGCTGATGATCCACATTTCCAGGGAAGAGGAAACAAGAGCAGTGGAGAT
         N  F  H  A  A  P  N  I  D  H  S  Q  E  F  V  R  N  D  L  K
1861  AATTTCCATGCAGCACCAAACATTGATCACTCCCAAGAGTTTGTGAGGAATGATCTTAAA
         E  W  L  C  W  M  R  K  E  V  G  Y  D  G  W  R  L  D  F  V
1921  GAATGGCTTTGCTGGATGAGAAAGGAAGTCGGCTACGATGGATGGAGACTTGACTTTGTT
         R  G  F  W  G  G  Y  V  K  D  Y  L  E  A  S  E  P  Y  F  A
1981  CGTGGTTTCTGGGGTGGATATGTCAAGGACTATTTGGAAGCAAGTGAACCATACTTTGCA
         V  G  E  Y  W  D  S  L  S  Y  T  Y  G  E  M  D  Y  N  Q  D
2041  GTAGGAGAGTACTGGGACTCCCTCAGTTATACTTATGGTGAAATGGACTACAATCAGGAT
         A  H  R  Q  R  I  V  D  W  I  N  A  T  N  G  T  A  G  A  F
2101  GCCCACAGGCAGAGAATTGTTGATTGGATAAATGCTACAAATGGAACTGCTGGCGCATTT
         D  V  T  T  K  G  I  L  H  A  A  L  E  R  S  E  Y  W  R  L
2161  GATGTTACCACTAAAGGAATACTTCATGCGGCGCTTGAAAGATCAGAGTATTGGCGCCTG
         S  D  E  K  G  K  P  P  G  V  L  G  W  W  P  S  R  A  V  T
2221  TCCGATGAAAAGGGAAACCCCCTGGAGTATTGGGTTGGTGGCCTTCAAGAGCAGTCACA
         F  I  E  N  H  D  T  G  S  T  Q  G  H  W  R  F  P  Y  G  M
2281  TTTATAGAGAATCATGATACTGGTTCTACTCAGGGCCATTGGAGGTTCCCCTATGGTATG
         E  L  Q  G  Y  A  Y  I  L  T  H  P  G  T  P  A  V  F  Y  D
2341  GAACTGCAAGGATACGCCTACATCCTGACACACCCTGGCACTCCCGCAGTCTTCTATGAC
         H  I  F  S  H  L  Q  P  E  I  A  K  F  I  S  I  R  H  R  Q
2401  CACATATTTTCACACTTACAACCAGAGATCGCTAAATTTATTTCCATTCGACACCGTCAA
         K  I  H  C  R  S  K  I  K  I  L  K  A  E  R  S  L  Y  A  A
2461  AAGATTCATTGCCGCAGCAAGATCAAGATACTAAAGGCAGAGAGGAGTTTATATGCGGCT
         E  I  D  E  K  V  T  M  K  I  G  S  E  H  F  E  P  S  G  P
2521  GAAATTGATGAGAAGGTAACAATGAAAATCGGATCAGAACATTTTGAGCCAAGCGGTCCC
         Q  N  W  I  V  A  A  E  G  Q  D  Y  K  I  W  E  A  S  *
2581  CAGAACTGGATTGTTGCTGCTGAGGGTCAAGATTACAAAATCTGGGAAGCGTCTTCATAG
```

*FIG. 9B*

Sequence alignment of large α-amylases

```
Zm_AMY3_partial  ---------------------------------------------------------------------
Os_AMY3          -MAVASWSIPAIPRAGPTARGVLLGGAFVTAARPP----VAWRCRATLPRRVRLG-----GVVARAGAAETP
At_AMY3_3        MSTVPIESLLHHSYLRHNSKVNRGNRSFIPISLNLRSHFTSNKLLHSIGKSVGVSSMNKSPVAIRATSSDTA
                 ........10........20........30........40........50........60........70.

Zm_AMY3_partial  ---------------------------------------------------------------------
Os_AMY3          VAGSGEAG-LLFSEKFPLRRSRTVEGKAWVRVDAEPDGEGKCKVVIGCDVEGKWVLHWGVSYDGEQGREWDQ
At_AMY3_3        VVETAQSDDVIFKEIFPVQRIEKAEGKIYVRLKEVK--EKNWELSVGCSIPGKWILHWGVSYGDTGSEWDQ
                 ........80........90........100.......110.......120.......130.......140.

Zm_AMY3_partial  ---------------------------------------------------------------------
Os_AMY3          PPSDMRPPGSVPIKDYAIETSLDTPHNSEGKTIHEVQIKIDKGTSIAAINFVLKVQILRCCILYHVSKGLEV
At_AMY3_3        PPEDMRPPGSIAIKDYAIETPLKK--LSEGDSFFEVAINLNLESSVAALNFVLK-----------------
                 ........150.......160.......170.......180.......190.......200.......210.

Zm_AMY3_partial  ---------------------------------------------------------------------
Os_AMY3          YDWPIRFVKLLKVPKEEETGAWFQHKGQDFRIPLSGSFG--GDLLGTEQDIDVRPGHLSNVLQKPEGPIAEP
At_AMY3_3        ------DEETGAWYQHKGRDFKVPLVDDVPDNGNLIGAKKGFG-ALGQLSNIPLKQDKSSAET
                 ........220.......230.......240.......250.......260.......270.......280.

Zm_AMY3_partial  -----------------------------------------------------------------360
Os_AMY3          HKTVPDDKGSRTKHISGFYEEYPILKTVYQNFITVNVRENNGTTKHAVEFDTDIPGEVIIHWGVCKDNTMT
At_AMY3_3        -DSIEERKG----LQEFYEEMPISKRVADDNSVSVTARKCPETSKNIVSIETDLPGDVTVHWGVCKNGTKK
                 .290.......300.......310.......320.......330.......340.......350.

Zm_AMY3_partial  ---------------------------------------------------------------------
Os_AMY3          WEIPPEHPPATKIFRQKALQTMLQQKADGTGNSLSFLLDGEYSGLIFVVKLDEYTWLRNVENGFDFYIPLT
At_AMY3_3        WEIPSEPYPEETSLFKNKALRTRLQRKDDGNGSFGLFSLDGKLEGLCFVLKLNENTWLN--YRGEDFYVPFL
                 ........370.......380.......390.......400.......410.......420.......430.

Zm_AMY3_partial  ---------------------------------------------------------------------
Os_AMY3          R--------ADAEADKQKADDKSSQD--DGLISDIRNLVVGLSSRRGQRAKNKVLQEDILQEIERLAAE
At_AMY3_3        TSSSSPVETEAAQVSKPKRKTDKEVSASGFTKEIITEIRNLAIDISSHKNQKTNVKEVQENILQEIEKLAAE
                 ........440.......450.......460.......470.......480.......490.......500.
```

FIG. 10A

```
Zm_AMY3_partial  ------------------------------------------------------------
Os_AMY3          AYSIFRSPTIDTVEESVYIDDSSIVKPACS-GTGSGFEILCQGFNWESHKSGKWYVELGSKAKELSSMGFTI
At_AMY3_3        AYSIFRSTTPAFSEEGVLEAEADKPDIKISSGTGSGFEILCQGFNWESNKSGRWYLELQEKADELASLGFTV
                 .....510........520........530........540........550........560........570....

Zm_AMY3_partial  ------------------------------------------------------------
Os_AMY3          VWSPPPTDSVSPEGYMPRDLYNLNSRYGTMEELKEAVKRFHEAGMKVLGDAVLNHRCAQFQNQGVWNIFGG
At_AMY3_3        LWLPPPTESVSPEGYMPKDLYNLNSRYGTIDELKDTVKKFHKVGIKVLGDAVLNHRCAHFKNQGVWNLFGG
                 ...580........590........600........610........620........630........640....

Zm_AMY3_partial  -------QGRGNKSSGDNFHAAPNIDHSQEFVRNDLKEWLCWMRKEVGYDGWRLDFVRGFWGG
Os_AMY3          RLNWDDRAVVADDPHFQGRGNKSSGDNFHAAPNIDHSQEFVRSDLKEWLCWMRKEVGYDGWRLDFVRGFWGG
At_AMY3_3        RLNWDDRAVVADDPHFQGRGNKSSGDNFHAAPNIDHSQDFVRKDIKEWLCWMMEEVGYDGWRLDFVRGFWGG
                 .650........660........670........680........690........700........710........720

Zm_AMY3_partial  YVKDYLEASEPYFAVGEYWDSLSYTYGEMDYNQDAHRQRIVDWINATNGTAGAFDVTTKGILHAALERSEYW
Os_AMY3          YVHDYLEASEPYFAVGEYWDSLSYTYGEMDYNQDAHRQRIVDWINATNGTAGAFDVTTKGILHSALERSEYW
At_AMY3_3        YVKDYMDASKPYFAVGEYWDSLSYTYGEMDYNQDAHRQRIVDWINATSGAAGAFDVTTKGILHTALQKCEYW
                 ...730........740........750........760........770........780........790

Zm_AMY3_partial  RLSDEKGKPPGVLGWPSISVTFIENHDTGSTQGHWRFPYGMELQGYAYILTHPGTPAVFYDHIFSHLQPEI
Os_AMY3          RLSDEKGKPPGVLGWPSISVTFIENHDTGSTQGHWRFPFGMELQGYVYILTHPGTPAIFYDHIFSHLQPEI
At_AMY3_3        RLSDPKGKPPGVGWPSRAVTFIENHDTGSTQGHWRFPEGKEMQGYAYILTHPGTPAVFFDHIFSDYHSEI
                 .....800........810........820........830........840........850........860..

Zm_AMY3_partial  AKFISIRHRQKIHCRSMIKILKAERSLYAAEIDEKVTMKIGSEHFEP-SGPQNWIVAAEGQDYKIWEASS
Os_AMY3          AKLISIRNRQKIHCRSKIKILKAEGNLYAAEIDERVTMKIGAGHFEP-SGPTNWVVAAEGQDYKVWEVSS
At_AMY3_3        AALLSLRNRQKLHCRSEVNIDKSERDVYAAIIDEKVAMKIGPGHYEPPNGSQNWSVAVEGRDYKVWETS-
                 ..870........880........890........900........910........920........930..
```

Target peptide    SEX 1 domains         α-amylase domain

Nt [══════][════════════════════][══════════════════════════════] Ct
   ~50 Aa      ~420Aa                      ~460Aa

FIG. 10B

IDENTIFICATION AND CHARACTERIZATION OF A NOVEL ALPHA-AMYLASE FROM MAIZE ENDOSPERM

CROSS REFERENCE TO RELATED APPLICATIONS

The present application is a divisional application of U.S. application Ser. No. 10/952,551 now matured into now U.S. Pat. No. 7,270,988 entitled IDENTIFICATION AND CHARACTERIZATION OF A NOVEL ALPHA-AMYLASE FROM MAIZE ENDOSPERM filed Sep. 27, 2004 and claims priority benefit of U.S. Provisional Application No. 60/505,995, filed Sep. 25, 2003, entitled IDENTIFICATION AND CHARACTERIZATION OF A NOVEL ALPHA-AMYLASE FROM MAIZE ENDOSPERM, the whole of which are hereby incorporated by reference herein.

STATEMENT REGARDING FEDERALLY SPONSORED RESEARCH OR DEVELOPMENT

N/A

BACKGROUND OF THE INVENTION

Starch is the major storage carbohydrate in higher plants. The biochemical mechanisms of starch biosynthesis and starch utilization are of interest for understanding fundamental aspects of plant physiology and also for their potential utility in manipulating the starch pathway for practical purposes. Not only is starch a critical primary source of dietary carbohydrates, but it is also used extensively for various industrial purposes ranging from formation of packaging materials to ethanol production. Despite its wide availability in nature and its many industrial applications, the mechanisms by which starch is formed and degraded in plant endosperm tissue are not well understood.

Starch consists essentially of a mixture of the homopolysaccharides amylose and amylopectin [11, 24]. Amylose is a linear chain of glucosyl units joined by alpha-1,4 glycosidic bonds and normally constitutes about 25% of the total endosperm starch in maize (*Zea mays*). Amylopectin comprises many linear chains of glucosyl monomers joined by alpha-1,4 linkages and constitutes approximately 75% of the starch. The chains of amylopectin are joined to each other by alpha-1,6 glycosidic bonds, often referred to as branch linkages. In amylopectin, the organized positioning of branch linkages enables periodic clustering of the linear chains [9, 15]. This permits tight and efficient packaging of glucose units, and confers crystallinity to the granule. The functional properties of starch relate directly to this architectural organization of linear chains and branch linkages in amylopectin [23].

The organization of amylopectin and amylose into higher order structures that lead to granule formation renders starch resistant to degradation. However, starch granules can be completely degraded by a combination of phosphorolysis and hydrolysis when glucose supply is required [2]. As no single enzyme has been shown to completely convert starch to simple sugars, multiple enzymes most likely are involved. Starch debranching enzymes and disproportionating enzymes are potential degradative enzymes, as are the alpha-1,4 linkage-specific hydrolases of the alpha-amylase and beta-amylase classes. Genetic evidence for involvement of an alpha-amylase in starch degradation comes from the sex4 mutant of *Arabidopsis*, which lacks such an enzyme and accumulates abnormally high levels of starch in leaves [34].

Another enzyme that likely participates in starch degradation is phosphorylase, which inserts phosphoryl groups from inorganic pyrophosphate into the alpha-1,4 glucoside bond, releasing glucose-1-phosphate.

Classification of starch degrading enzymes is made according to their behavior: endo- versus exo-mode of attack, inversion versus retention of anomeric configuration of the substrate, preference for length of the glucosyl chain, preference for the nature of the glucosyl bond, and hydrolytic versus glucosyl-transfer activity [31]. Alpha-amylases are endo-acting hydrolytic enzymes that hydrolyze internal alpha-1,4 linkages in alpha D-glucan polymers, such as amylopectin and amylose molecules. Alpha-amylases are widely distributed in nature, and are produced by plants, animals, and microorganisms [28]. Those from different sources are known to have different substrate specificities, acting preferentially on glucan chains of different lengths. This substrate specificity is dependent on the configuration of the active site of the enzyme and results in characteristic products that are formed according to the enzyme source [28]. For example, salivary gland and pancreatic alpha-amylases immediately produce low molecular weight products such as maltose and maltotriose by "multiple attack" on the substrate [27], and barley alpha-amylase primarily produces maltose, maltohexaose, and maltoheptaose without multiple attack [19]. Because alpha-amylases can hydrolyze linkages only so close to a branch point (generated by an alpha-1,6 linkage), activity halts when this physical limitation occurs. When hydrolytic activity of the alpha-amylase reaches this limit, the resulting product is termed a "limit dextrin". To achieve further hydrolysis of the limit dextrin, other enzymes must be employed, such as exo-cleaving beta-amylases or debranching enzymes. All of the alpha-amylase activities that have been described to date hydrolyze alpha D-glucans to maltose, maltotriose, or other small malto-oligosaccharides plus alpha-limit dextrins of various sizes [19, 28, 31].

Hydrolysis of starch with alpha-amylases from bacteria or fungi is routinely used by some starch industries as a first step in the process of the complete degradation of starch to glucose (this step is termed "saccharification"). The hydrolysis of starch to glucose is preliminary to the manufacture of conversion products such as high fructose corn syrup or fuel ethanol [18]. The goal of other starch processing industries is the incomplete hydrolysis of starch by various degradative enzymes, including alpha-amylases, to generate limit dextrins (termed "maltodextrins") in a range of sizes that are used for a variety of industrial purposes. For example, maltodextrins are used in food and pharmaceutical manufacturing as thickening agents, cryoprotectants and binders. They can also be further processed or chemically modified for use as viscosity or hygroscopicity or dissolving agents [13]. Different limit dextrin products are typically produced by varying the combination of enzymes used for the starch digestion, or by varying the digestion conditions. An important industrial goal is the low-energy production of specific starch hydrolysates containing few by-products [18].

In plants, alpha-amylases are believed to be involved in the hydrolysis of transient starch in the leaves, which occurs during the dark cycle of the plant, and in the hydrolysis of storage starch that accumulates in seeds or tubers, which occurs during seed germination or tuber sprouting. The first complete sequence of a plant genome, that of the *Arabidopsis* genome, reveals that three alpha-amylase genes are present in this plant species [14, 16]. Two are genes that encode predicted polypeptides of approximately 50-60 kilodaltons (kD), and one is a gene that encodes a larger form predicted to have a molecular mass of approximately 100 kD (Genbank Accession No. NM_105651). Sequencing of the rice genome reveals the presence of one homolog of the *Arabidopsis* gene that encodes the large alpha amylase [12]. This rice gene is also predicted to encode a polypeptide of approximately 100 kD (Genbank Accession No. AP003408). In addition, the rice genome contains several genes that code for smaller sized (50-60 kD) alpha-amylases. All of the plant 50-60 kD alpha-amylases are similar in size to those from bacteria, yeast, and mammals that are used commercially. Activities of the 50-60 kD alpha-amylase enzymes from plants also are similar to those of bacterial, fungal, and mammalian alpha-amylase enzymes, in that they result in starch hydrolysis products consisting of maltose, maltotriose, or small oligosaccharides plus alpha limit dextrins. The activities of the 100 kD plant alpha-amylases and the nature of their starch hydrolysis products have not been characterized to date.

Alignment of the amino acid residues of all predicted alpha-amylases (both large and small) reveals they are highly similar in their C-terminal regions, which are believed to contain the catalytic domain of the protein [17]. The two 100 kD alpha-amylases from *Arabidopsis* and rice also have considerable amino acid sequence similarity, with 37% sequence identity in their N-terminal regions and 59% amino acid identity overall. The N-termini of the *Arabidopsis* and rice 100 kD alpha-amylases also have two small regions of similarity with another protein from *Arabidopsis* that has been termed the R1-protein, the product of the sex1 gene [26, 35]. Mutations in the sex1 gene result in excess starch accumulation, suggesting that a functional R1-protein is required for starch degradation. This suggests the larger 100 kD alpha-amylases from plants comprise a distinct isoform class of alpha-amylase enzymes. Further investigation into the role of the large alpha-amylase in starch metabolism, particularly in an agronomically important plant such as maize, is desirable.

BRIEF SUMMARY OF THE INVENTION

The invention is based on the discovery of a novel starch hydrolytic activity (called Starch Hydrolytic Enzyme, or SHE) in developing maize kernels. The specificity of native, purified SHE is similar, in general terms, to previously known alpha-amylases since both activities are able to hydrolyze starch, amylopectin, amylose, and beta-limit dextrin but are not able to hydrolyze the branched polymer pullulan. However, the activity of SHE toward amylopectin results in hydrolysis products that are distinctly different from those of other alpha-amylases. Specifically, they are of the same approximate molecular mass as beta-limit dextrins and do not include maltose or malto-oligosaccharides. This unique activity suggests that the novel maize alpha-amylase is an endo-hydrolytic enzyme that specifically cleaves long amylopectin chains ($B_2$ or $B_3$ chains) that extend between unit clusters in the molecule. In contrast, conventional maize amylases, in addition, clip off the smaller side chains of amylopectin. The new enzyme according to the invention, SHE, and its homologous equivalents in other plants such as rice, *Arabidopsis*, apple and potato, will have value in starch processing for generating different, and perhaps larger sized, alpha-limit dextrins for industrial use, as compared to those generated by previously known alpha-amylases or other starch hydrolytic enzymes. In addition, modification of the expression of this enzyme in transgenic maize plants or in other transgenic organisms (including bacteria, yeast, and other plant species) can be useful for the generation of novel starch forms or altered starch metabolism.

The cDNA encoding the new enzyme according to the invention, SHE, has also been isolated and sequenced. cDNA sequences encoding SHE or portions thereof can be incorporated into replicable expression vectors and the vectors transfected into an appropriate host (e.g., bacterial, yeast, eucaryotic cell culture). Alternatively, genomic DNA fragments encoding SHE can be utilized in situ. The SHE protein, in either naturally occurring or recombinant form, can be used in the starch processing industry or in other industries that employ starch for any purpose. The protein, or fragments thereof, also can be employed as an immunogen in order to raise antibodies against SHE.

Thus, the invention generally features a Starch Hydrolytic Enzyme, SHE, or portions thereof; nucleic acid isolates encoding SHE or portions thereof; methods of producing SHE or portions thereof; cells transformed with a recombinant vector containing a SHE-encoding alpha-amylase3 (Amy3) gene; antibodies to SHE or fragments thereof and methods to produce such antibodies; transgenic plants containing a SHE gene and methods to produce such transgenic plants; and methods of using a protein having SHE hydrolytic activity for starch degradation.

The invention also features a nucleic acid isolate able to hybridize under stringent conditions to the complement of a nucleic acid sequence encoding SHE, and the protein or polypeptide fragment, e.g., immunogenic fragment, thereof encoded by the nucleic acid isolate. The invention, furthermore, features a recombinant expression vector comprising a nucleic acid isolate able to hybridize under stringent conditions to the complement of a sequence encoding SHE, cells transformed with the recombinant expression vector, and methods of expressing the SHE protein or polypeptide fragment encoded within the recombinant expression vector.

Also featured is a method of producing the SHE protein, or polypeptide fragment thereof, comprising transforming a host cell with a nucleic acid able to hybridize under stringent conditions to a nucleic acid sequence encoding the SHE protein and linked to a nucleic acid sequence under the control of an inducible promotor, and inducing the cell to produce a fusion protein comprising the SHE protein, or polypeptide fragment thereof. The invention also features a SHE fusion protein, methods of producing antibodies to a SHE fusion protein and antibodies produced by such method.

As used herein, the terms "isolated" or "purified" refer to a nucleic acid or protein sequence that has been separated or isolated from the environment in which it was prepared or in which it naturally occurs. Such nucleic acid or protein sequences may be in the form of chimeric hybrids or fusions, useful for combining the function of the nucleic acid or protein sequences of the invention with other species and also include recombinant forms. The term "determinant" as used herein includes the site on an antigen at which a given antibody molecule binds. The term "immunogenic fragment" refers to a fragment of SHE protein that reacts with antibodies specific for a determinant of SHE.

The SHE protein can be used as an alternative hydrolase, along with bacterial and fungal starch hydrolases and debranching enzymes, for industrial starch processing applications. SHE-encoding cDNA (Amy3), SHE-encoding genomic DNA (Amy3), or portions thereof may be utilized as markers for the identification of specific corn varieties, and for the development of corn varieties with starch properties tailored for specific industrial applications. Amy3 cDNA or genomic DNA fragments can be used to produce these proteins or peptide fragments or as probes to identify nucleic acid molecules encoding related proteins or polypeptides (e.g., homologous polypeptides from related species and heterologous molecules from the same species). Assays for SHE function, production or expression by cells are made possible by the development of antibodies reactive with the SHE protein.

BRIEF DESCRIPTION OF THE SEVERAL VIEWS OF THE DRAWINGS

Other features and advantages of the invention will be apparent from the following description of the preferred embodiments thereof and from the claims, taken in conjunction with the accompanying drawings in which:

FIG. 8 is a chart showing the results of MALDI-TOF analysis of tryptic peptides produced from digestion of the 94 kD form of SHE;

FIGS. 9A and 9B show the nucleotide sequence of ZmAmy3 cDNA (SEQ ID NO: 1) aligned with the amino acid sequence (single letter code) of the encoded SHE protein (SEQ ID NO: 2), according to the invention;

FIGS. 10A and 10B show a sequence alignment of the SHE protein according to the invention (SEQ ID NO: 2) with the predicted polypeptide sequences for both the rice (SEQ ID NO: 15) and the *Arabidopsis* 100 kD alpha-amylases (AMY3) (SEQ ID NO: 16)

DETAILED DESCRIPTION OF THE INVENTION

Figure 1:
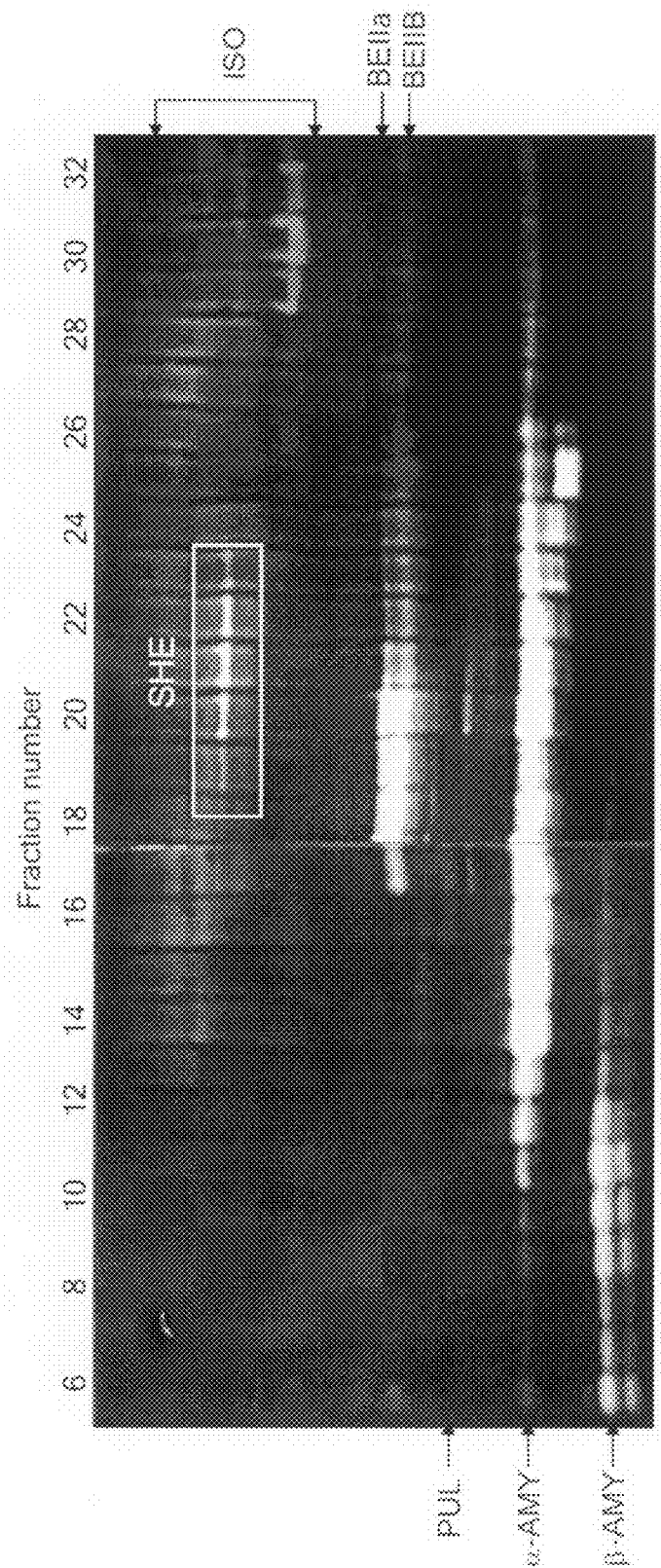
FIG. 1 is a gel showing two-dimensional separation of starch-metabolizing enzymes from developing maize endosperm.

Two-dimensional native PAGE/activity gel analysis (i.e., starch zymogram analysis) of proteins from developing maize kernels harvested 20 days after pollination (DAP) was used to identify a novel maize starch hydrolytic activity. As shown in FIG. 1, proteins in specific anion exchange chromatography fractions were separated by electrophoresis through a native polyacrylamide gel and then transferred to another polyacrylamide gel containing starch. Enzymatic activity that altered the starch substrate in the gel was visualized by staining with iodine solution. A distinct white activity band indicating starch hydrolysis, and not correlated with the activity of known starch hydrolytic enzymes, was identified in chromatography fractions 19-23.

Figure 2:
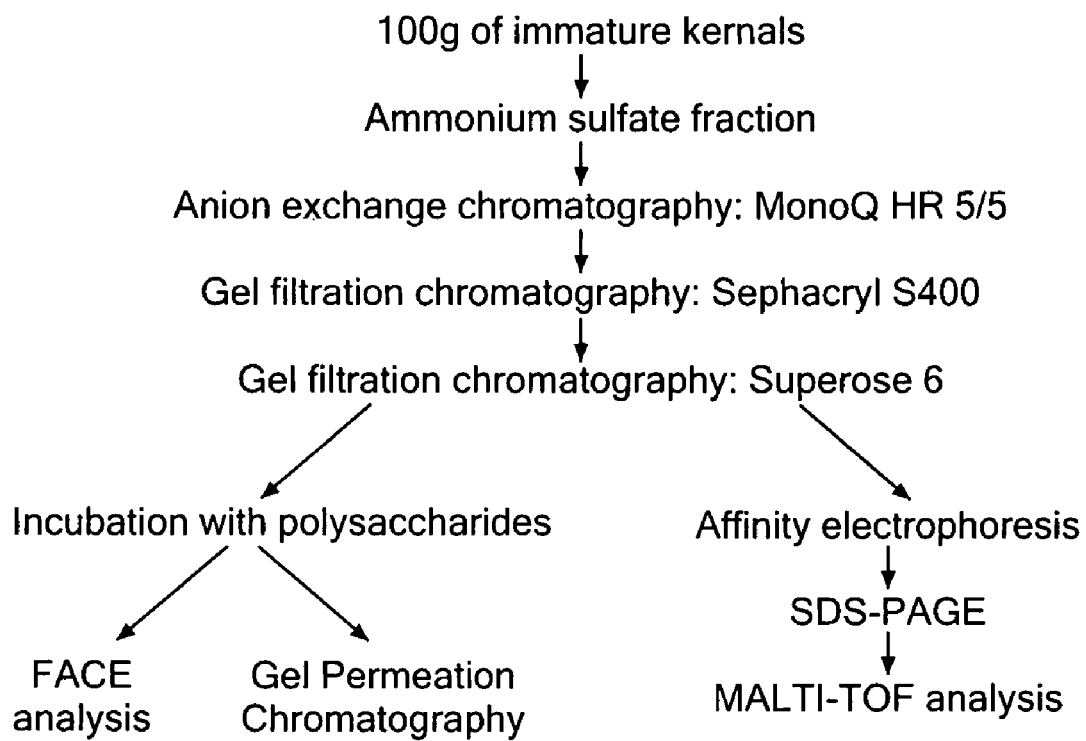
FIG. 2 is a flow chart showing a purification scheme for purifying the Starch Hydrolytic Enzyme (SHE) according to the invention.

This newly identified enzymatic activity was specifically isolated in a series of purification steps, including ammonium sulfate precipitation, anion exchange chromatography, gel permeation chromatography and affinity electrophoresis, as diagramed in FIG. 2. These purification steps resulted in a preparation of the enzyme that was devoid of other starch metabolizing activities. Those fractions containing purified SHE activity were pooled and used to carry out various incubation experiments with different polysaccharide substrates.

Figure 3:
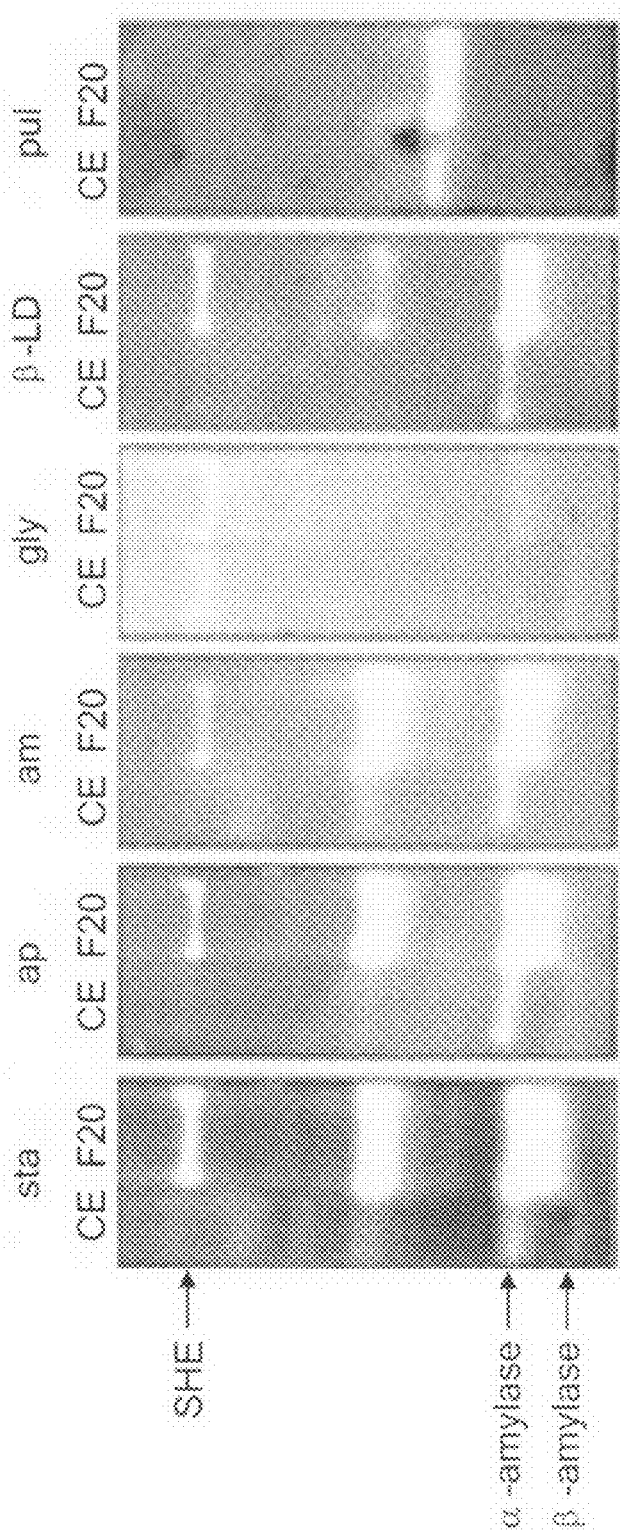
FIG. 3 is a gel analysis of hydrolysis results showing the specificity of SHE toward different polysaccharides.

The glucan substrate specificity of this novel enzyme, called here Starch Hydrolytic Enzyme (SHE), was determined by zymogram analysis. As shown in FIG. 3, the specificity of SHE is similar, in general terms, to that of previously known alpha-amylases. Both activities are able to hydrolyze starch (Sta), amylopectin (Ap), amylose (Am) and the beta-limit dextrin of amylopectin (β-LD), but they are not able to hydrolyze the branched isomaltotriose polymer called pullulan (Pul).

Figure 4A:
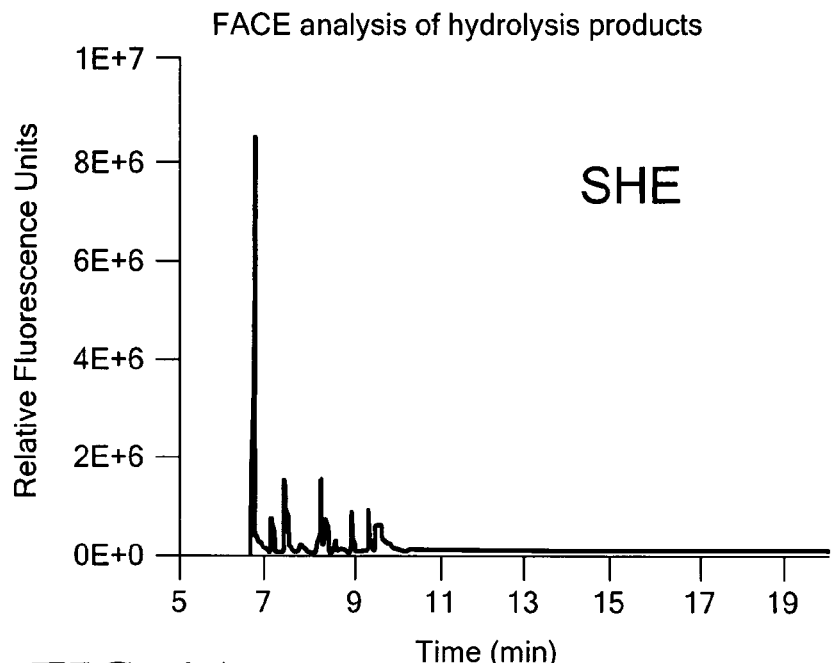
FIGS. 4A and 4B are graphs showing FACE analysis of hydrolysis products of amylopectin incubated with SHE (FIG. 4A) and a conventional alpha-amylase (FIG. 4B)
Figure 4B:
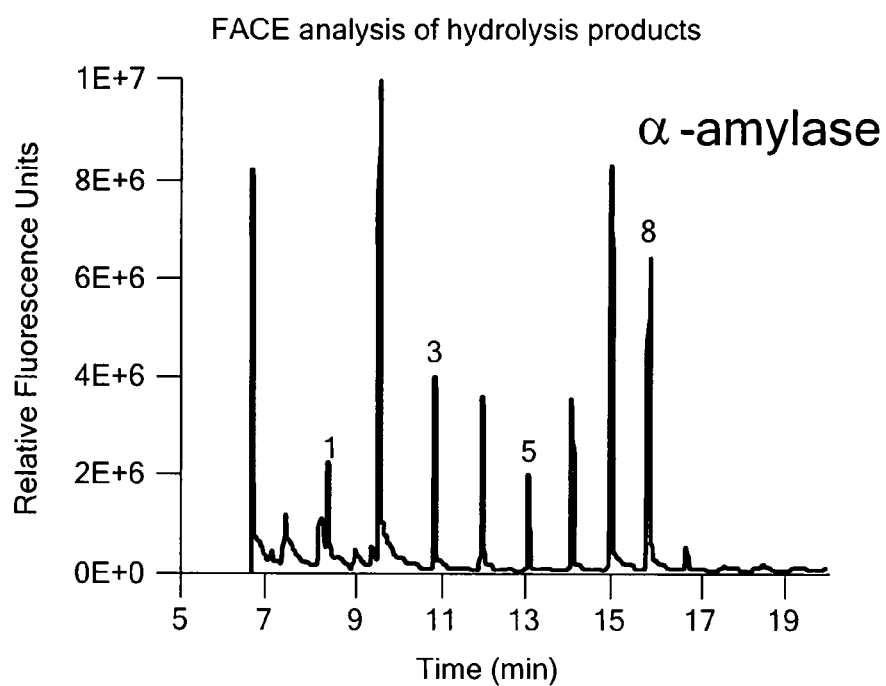

Differences between SHE activity and that of conventional alpha-amylases were detected, however, after extended incubation of the purified SHE protein with starch, amylopectin, and beta-limit dextrin. Each individual substrate was incubated overnight with SHE or with a lower molecular weight alpha-amylase similarly purified from the same maize endosperm tissue (a "conventional" alpha-amylase). The hydrolysis products were analyzed by fluorophore-assisted capillary electrophoresis (FACE) [7, 25]. As indicated in FIG. 4A, SHE activity does not release small oligosaccharides (i.e., short chains consisting of 1 to 8 units of glucose), in contrast to the activity of the conventional maize alpha-amylase (FIG. 4B).

Figure 5:
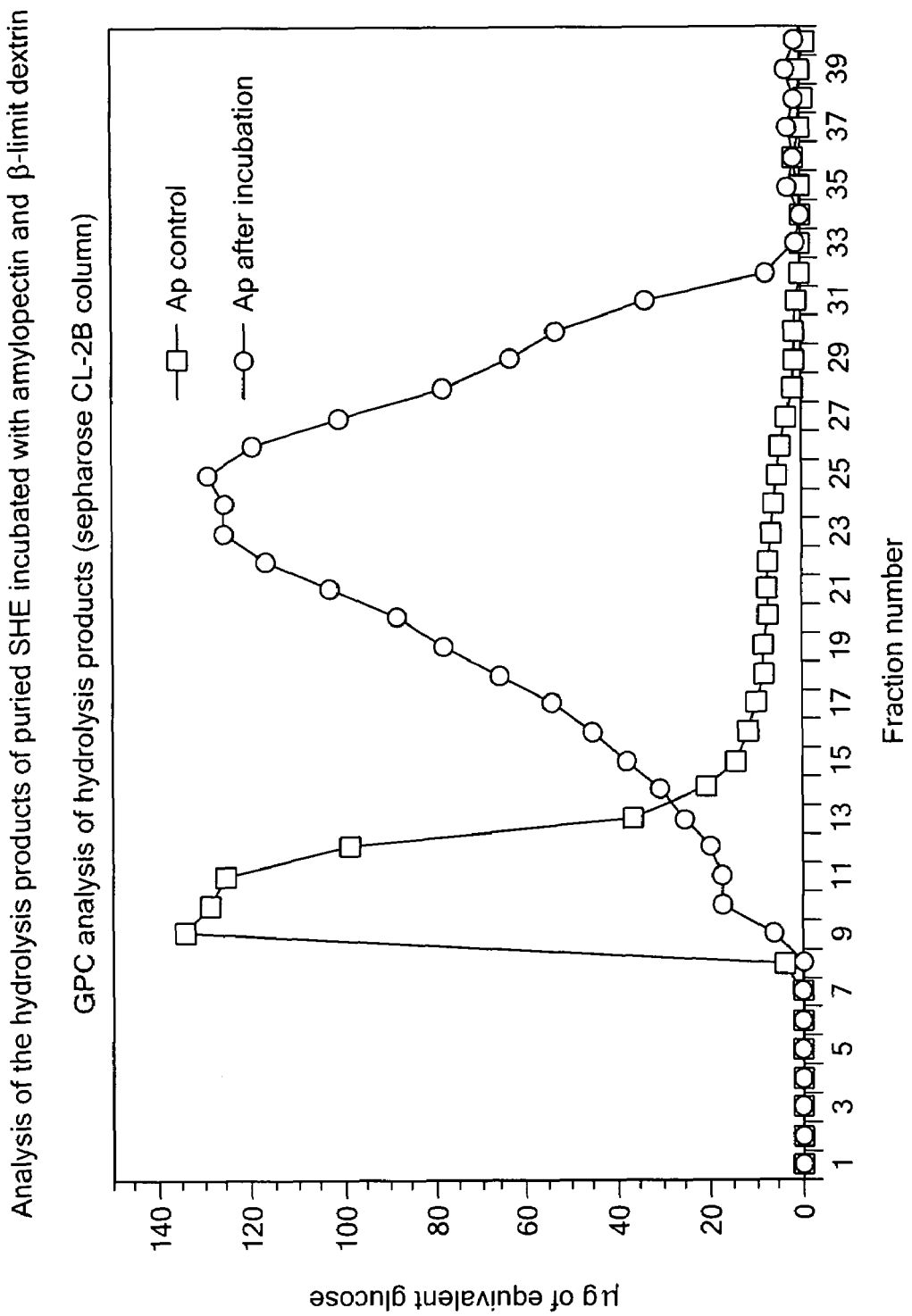
FIG. 5 is a graph showing GPG analysis (Sepharose CL-2B column) of the hydrolysis products of amylopectin incubated with purified SHE.
Figure 6:
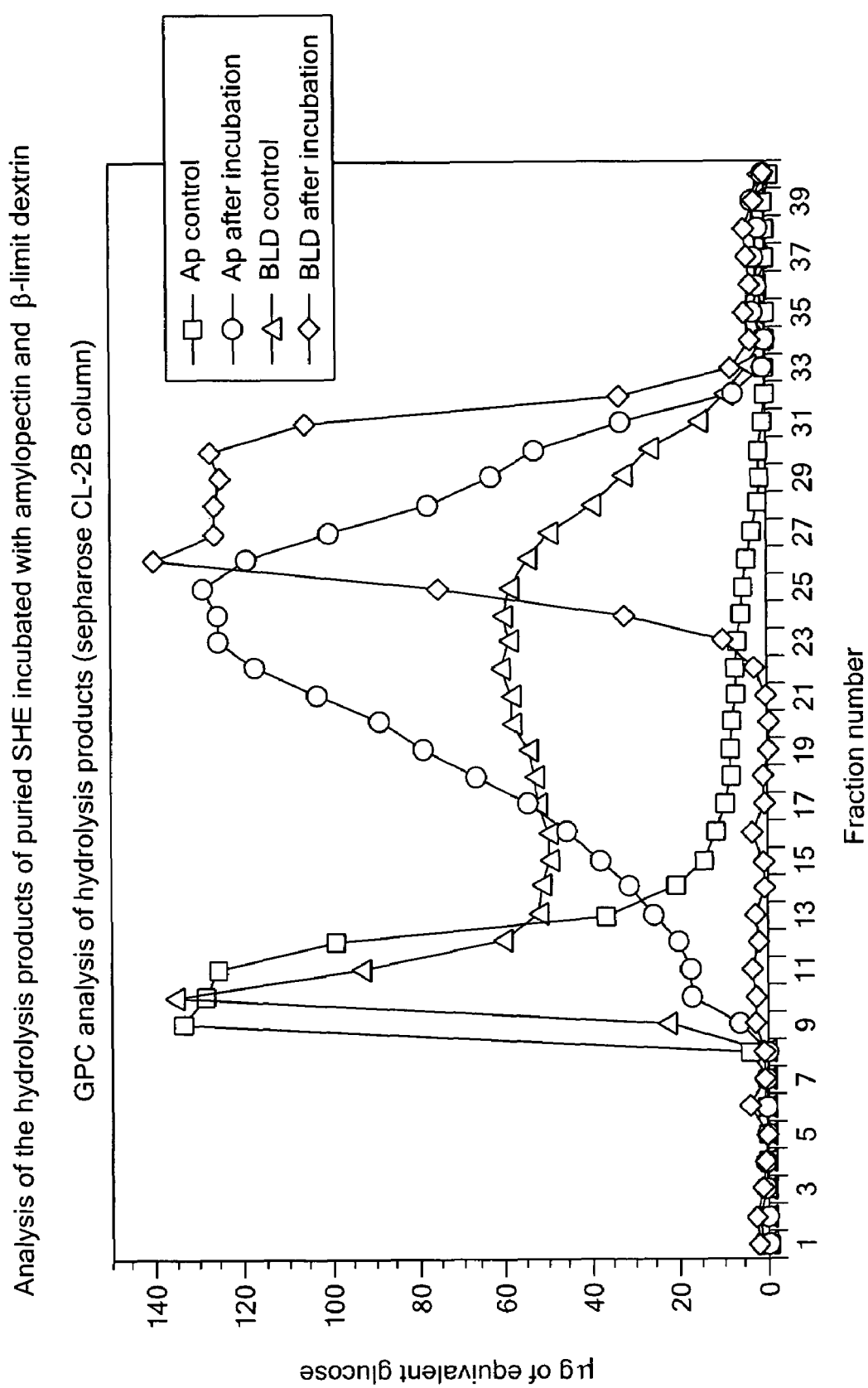
FIG. 6 is a graph showing GPG analysis (Sepharose CL-2B column) of the hydrolysis products of beta-limit dextrin incubated with purified SHE, overlaid on the graph of FIG. 5.

The hydrolysis products were further characterized by gel permeation chromatography on a Sepharose CL-2B column. FIG. 5 displays the analysis of hydrolysis products that resulted from the incubation of amylopectin with purified SHE. In addition, FIG. 6 compares the analysis of FIG. 5 with that of hydrolysis products resulting from the incubation of beta-limit dextrin with SHE. These experiments demonstrate that purified SHE activity hydrolyzes both branched polysaccharides, as indicated by significant decreases in the molecular mass of each. However, the results also indicate that the hydrolysis products themselves are of high molecular weight, because no short glucosyl chains were detected by the FACE analysis (see FIG. 4).

The apparent molecular weight of SHE was determined by gel permeation chromatography following passage of the purified protein over a Superose-6 column. Comparison of the migration of the activity to that of known molecular weight standards provided the estimate that SHE is approximately 366 kD (FIG. 7A). However, analysis of purified SHE under denaturing conditions by SDS-PAGE, followed by staining with Coomassie-Blue (FIG. 7B), revealed that the molecular weight of the SHE polypeptide monomer is approximately 94 kD. This suggests that the purified SHE activity results from the formation of an enzyme complex that most likely is comprised of four SHE subunits.

Figure 7B:
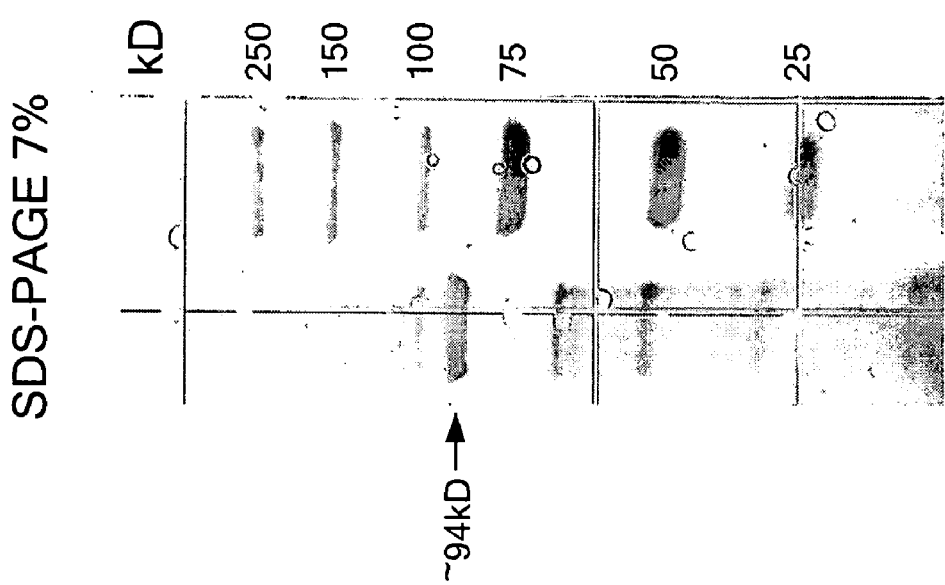
FIG. 7B is a gel showing a molecular weight determination of SHE under denaturing conditions by SDS-PAGE 7% analysis.
Figure 7A:
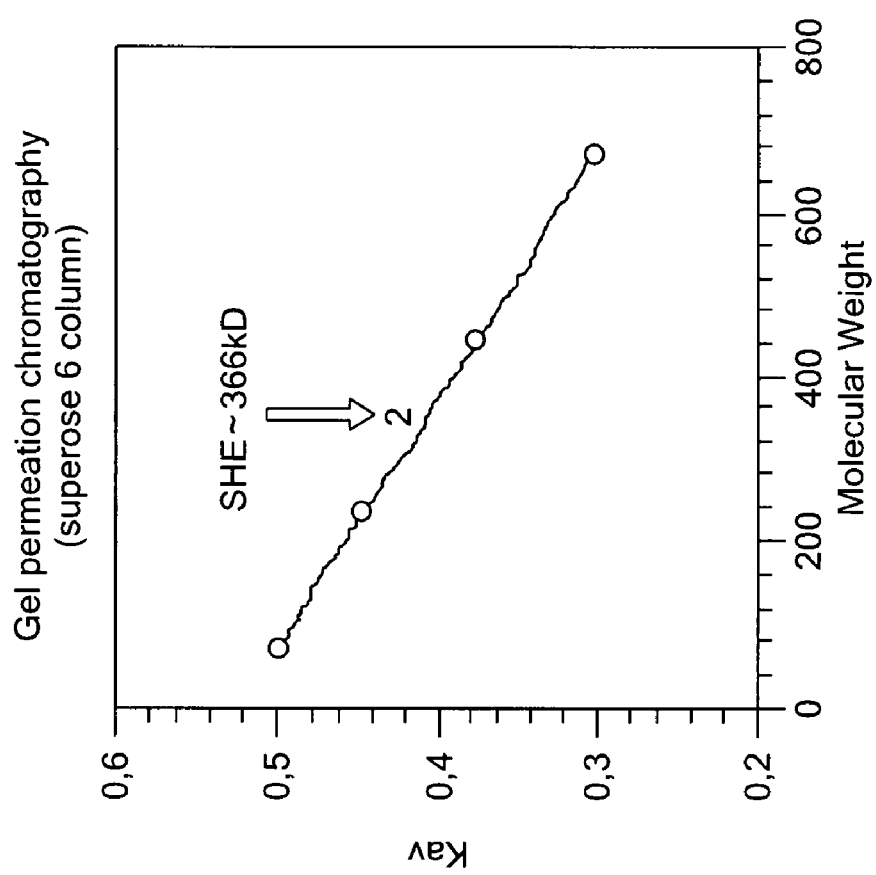
FIG. 7A is a graph showing GPC determination (Superose 6 column) of the molecular weight of SHE under native conditions.

The identity of the purified protein shown in FIG. 7B was established by subjecting the 94 kD polypeptide to mass spectrometric analysis (MALDI-TOF) following trypsin digestion. The mass of each tryptic peptide was determined, and these were compared to the masses of tryptic peptides of all known proteins available in the databases. Database analysis determined that the protein identity is closest to that of the 100 kD alpha-amylase that is the predicted product of the rice large alpha-amylase gene (AMY3)(Genbank AP003408) (FIG. 8).

Based on the results of the mass spectrophotometric analysis, the rice Amy3 gene sequence was used to search the Maize Gene Database for similar sequences. This database contains a partial sequence of the maize genome, including "expressed sequence tags" (ESTs) representing partial gene sequences. The database search uncovered a partial maize polypeptide sequence predicted from a 548 nt EST sequence (Genbank PCO139185) that closely matches the predicted polypeptide sequences for both the rice and the *Arabidopsis* 100 kD alpha-amylases (Atlg69830), as shown in FIG. 10.

The full-length coding sequence for the maize Amy3 (ZmAmy3) cDNA was PCR amplified using gene-specific primers complementary to the 3' end of the maize EST and degenerate primers based on the 5' region of the rice Amy3 gene sequence. The 2640 bp ZmAmy3 cDNA product (FIGS. 9A and 9B, SEQ ID NO.:1) is predicted to code for a polypeptide of approximately 99 kDa (SHE) (FIGS. 9A and 9B, SEQ ID NO.:2). At the amino acid level, the maize and rice sequences are 97% identical over the length of the polypeptide fragment predicted from the maize EST, and at the nucleic acid level the maize and rice sequences are 86% identical for this region. This high degree of sequence identity indicates that the maize EST derives from the maize Amy3 gene and that the purified SHE protein and the predicted rice AMY3 protein are homologous.

Comparisons of the deduced, full-length SHE amino acid sequence with the corresponding AMY3 sequences from rice and *Arabidopsis* revealed that all three large alpha-amylase polypeptides are closely conserved. Overall, the maize SHE sequence has 79% identity with the rice AMY3 polypeptide and 62% identity with the *Arabidopsis* AMY3 polypeptide. The rice and *Arabidopsis* AMY3 amino acid sequences are 59% identical. In the N-terminal regions, the rice and maize AMY3 polypeptides are 60% identical. Because the three known AMY3 polypeptides (including maize SHE) also have high sequence similarity to 50-60 kD AMY1 and AMY2 sequences from rice, *Arabidopsis*, and maize at their C-termini, they represent divergent plant alpha-amylase isoforms. The enzymatic activity of this class of alpha-amylase isoforms (AMY3) has not been characterized to date.

Use

The starch hydrolytic activity from maize kernels (SHE) described herein exhibits a novel alpha-amylase activity. As indicated above, the activity of this enzyme toward amylopectin results in hydrolysis products that are of the same approximate molecular mass as beta-limit dextrins. However, SHE activity does not result in the production of maltose or malto-oligosaccharides, as would be expected from any known, conventional alpha-amylase. This unique activity suggests that SHE is an endo-hydrolytic enzyme that specifically cleaves long amylopectin chains ($B_2$ or $B_3$ chains) that extend between unit clusters in the molecule, thus generating larger sized alpha-limit dextrins.

Figure 11:
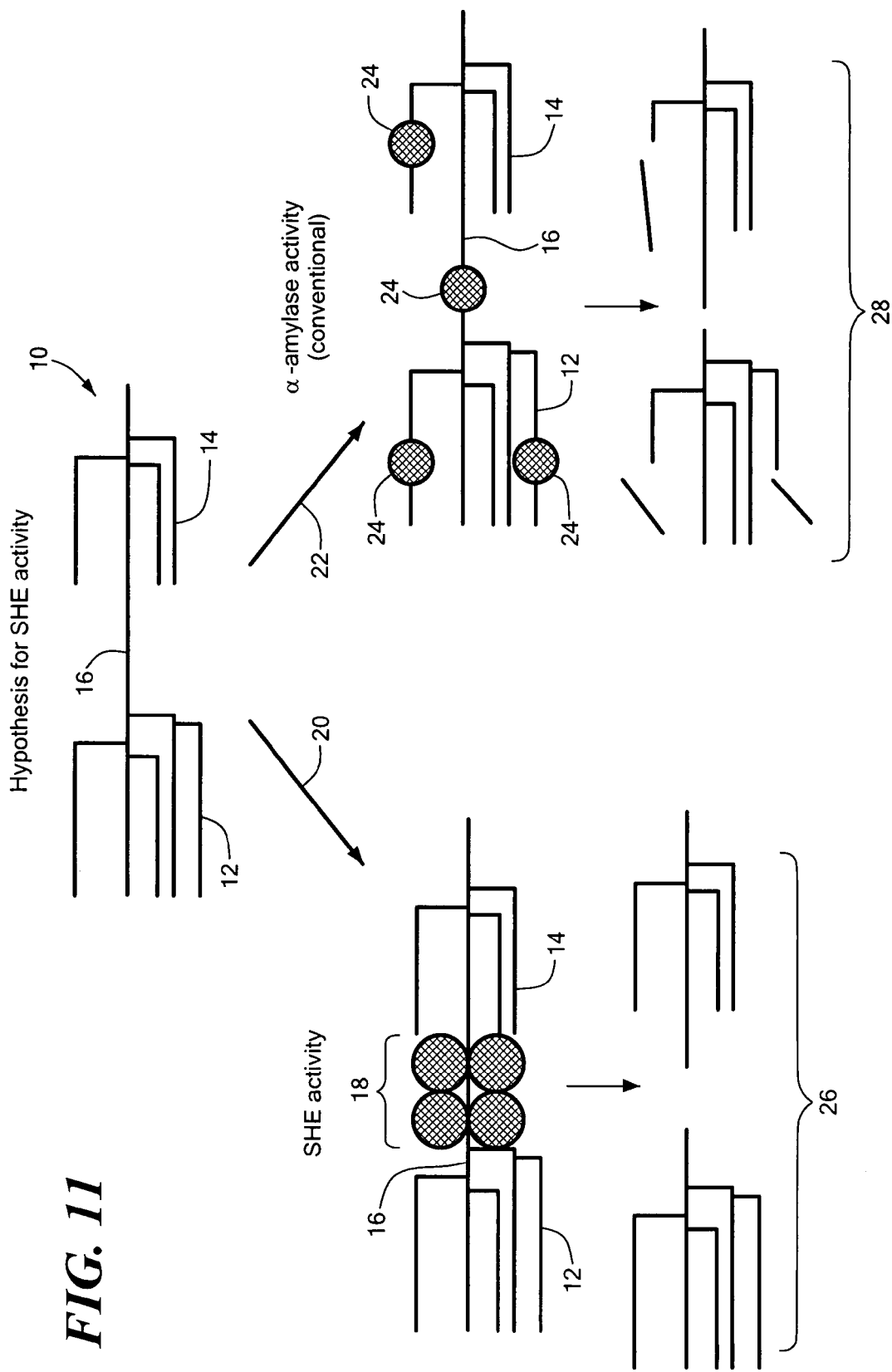
FIG. 11 shows a hypothetical reaction mechanism for SHE activity.

Referring to FIG. 11, a typical branched glucan substrate such as amylopectin 10, in which branch chains are arranged in distinct clusters 12, 14 connected by single (non-branched) $B_2$ or $B_3$ chains 16, would be acted upon differently by SHE and a conventional alpha-amylase. According to this model, SHE, by virtue of its assembly state and size (a 366 kD tetramer 18), would be barred from access (pathway 20) to the glucan chains in the interior regions of amylopectin, clusters 12, 14. Thus, SHE hydrolysis would be limited only to those regions of the amylopectin molecule that are accessible to the enzyme, for example the long linear chains 16 that extend between individual cluster units. No other enzyme is known that cleaves starch specifically in regions external to the unit clusters, producing larger sized alpha-limit dextrins 26. This is in stark contrast to the action (pathway 22) of conventional, smaller sized alpha-amylases, which function as monomers 24 and are likely to penetrate all regions of the amylopectin molecule, producing a mixture of small oligosaccharides and larger products 28.

Use of the ZmAmy3 cDNA that encodes SHE will make possible the isolation of active portions of SHE protein and, thus, the development of highly active, recombinant enzyme preparations for starch processing. In addition, ZmAmy3 cDNA can be used to isolate the cDNA encoding the homologous AMY3 enzymes from other plants with important starch hydrolytic pathways, such as rice, *Arabidopsis*, apple and potato.

As indicated above, recombinant SHE and/or the native maize enzyme, recombinant AMY3 enzymes from other plant species and active fragments thereof will have value in starch processing for consistently generating different, larger sized alpha-limit dextrins (maltodextrins) for industrial use. In comparison, the previously known alpha-amylases could be used to generate larger sized alpha-limit dextrins only by manipulating enzyme concentrations and/or incubation times, reaction conditions that could not be counted on to consistently produce the same products from batch to batch.

These new maltodextrin products will have value in food production as thickeners, emulsifiers, ice crystal retardants, texturizing agents, and/or fat or oil substitutes [13]. In manufacturing and pharmaceutical industries, the new maltodextrin products of SHE hydrolysis will have value as coating or encapsulation agents (e.g., for tablets or drug delivery), or as adhesive or binding agents.

The new enzyme according to the invention, SHE, and its homologous equivalents also will have value for the production of high MW dextrins that can potentially be used for the manufacture of biopolymers. Native and destructured starches have long been employed as particulate fillers and in commodity plastics [33]. Biopolymer blends containing either chemically modified or native starch forms are continually being examined for their effectiveness as packaging materials and biomedical adhesive agents [8, 22]. Large maltodextrins, such as those produced by SHE, may confer altered tensile properties and reduced water sensitivity to biopolymer blends.

Furthermore, the new enzyme according to the invention, SHE, and its homologous equivalents will have value as unique enzymes that can be added to formulations designed to selectively degrade starch. In addition, modification of the expression of the SHE enzyme and/or its homologous forms in transgenic maize plants or in other transgenic organisms (including bacteria, yeast, and other plant species) can be useful for the generation of novel starch forms or altered starch metabolism.

EXPERIMENTAL PROCEDURES

Maize Stocks and Allele Nomenclature

Wild type maize inbred lines in the W64A or the Oh43 inbred genetic backgrounds are used for analysis. Kernels are harvested 19-21 days after pollination (DAP), quick frozen in liquid nitrogen, and stored at −80° C. Prior to protein extraction, endosperm tissue is separated from embryo and pericarp tissues.

The nomenclature follows the standard maize (*Zea mays* L.) genetics format [1]. Names and symbols of genetic loci are italicized. Messenger RNAs and cDNAs are designated by italic font with the first letter capitalized, whereas polypeptide symbols are not italicized and are in upper case letters.

Species designations for orthologous loci are distinguished by having the first letter of both the genus and the species precede the locus designation (e.g., ZmAmy3 designates the *Zea mays* Amy3 cDNA).

Protein Extraction and Activity Gel Analysis

Protein isolation from endosperm is as described [7]. Briefly, frozen kernels (5 g) are ground to a fine powder in liquid nitrogen with a mortar and pestle, and the tissue is suspended in 5 mL of buffer containing 50 mM sodium acetate, pH 6, and 20 mM DTT. All of the lysates are centrifuged at 50,000 g for one hour at 4° C. Protein concentrations are determined according to the method of Bradford [3, 4].

For one-dimensional native PAGE activity gel analysis (i.e., zymogram analysis), total proteins (approximately 100 μg) are separated on a native polyacrylamide gel (16 cm×20 cm×0.15 cm). The resolving gel contains 7% (w/v) acrylamide (29:1 acrylamide-bisacrylamide [Sigma]) and 375 mM Tris-HCl, pH 8.8. The stacking gel contains 4% (w/v) acrylamide and 63 mM Tris-HCl, pH 6.8. Electrophoresis is conducted at 4° C., 25 V cm$^{-1}$ for 4 h using a Protean II cell (Bio-Rad) in an electrode buffer of 25 mM Tris, 192 mM glycine, pH 8.8, and 2 mM DTT. At the end of the run, the gel is electroblotted to a polacrylamide gel of the same size containing 7% acrylamide, 0.3% (w/v) potato starch (Sigma), and 375 mM Tris-HCl, pH 8.8. Alternative substrates to starch in the transfer gel include 0.3% (w/v) amylopectin (Sigma), 0.3% (w/v) amylose (Sigma), 0.3% (w/v) beta limit-dextrin (Megazyme), 0.3% (w/v) oyster glycogen (Sigma), and 0.3% (w/v) azure pullulan (Sigma). The transfer is performed overnight at 20 V in the electrode buffer at room temperature. Starch metabolic activities are observed by staining the gel with $I_2$/KI solution, and the gel is photographed immediately.

For two-dimensional zymogram analysis, total proteins (40 μg) are extracted as described above and loaded onto an anion exchange chromatography (MonoQ HR 5/5) using AKTA FPLC instrumentation (Amersham-Pharmacia). The MonoQ column is equilibrated with buffer A (50 mM Tris-acetate, pH 7.5; 10 mM DTT). Bound proteins are eluted with a 48 mL-linear gradient of 0 to 500 mM NaCl in buffer A containing 1M NaCl. The flow rate is 0.9 mL/min, and 1 mL fractions are collected. Proteins in each fraction are separated by non-denaturing PAGE. Following electrophoresis, proteins are transferred by electroblotting to a polyacrylamide gel of the same size containing 0.3% (w/v) starch. Starch metabolic activities are observed after staining the gel with $I_2$/KI solution, as described [7]. Transfer is performed overnight as described for the one-dimensional zymogram.

Protein Purification

The unknown glucan hydrolytic activity (termed "SHE") detected by one- and two-dimensional native PAGE activity gel analysis was purified in a step-wise manner from crude protein extracts isolated from approximately 100 grams mid-development maize kernels. At the conclusion of each purification step, starch zymogram analysis was employed to identify the fraction(s) containing SHE activity. The first step in the purification scheme was fractionation by ammonium sulfate precipitation, in which proteins were precipitated by the slow addition of saturated ammonium sulfate to 40% saturation. After incubation at 0° C. for 30 min, proteins were collected by centrifugation at 20,000 g for 20 min. The protein pellet was dissolved in 5 mL Buffer A and dialyzed twice against 400 mL Buffer A, according to previously described methods [5].

Dialyzed proteins were injected onto a FPLC MonoQ HR 5/5 column using AKTA FPLC instrumentation (Amersham-Pharmacia), preincubated with Buffer A. Bound proteins were eluted with a 48 mL-linear gradient of 0 to 500 mM NaCl in buffer A containing 1M NaCl. The flow rate was 0.9 mL/min, and 1 mL fractions were collected. MonoQ fractions containing SHE activity were pooled and further purified by gel filtration chromatography (GPC) on a Sephacryl S400 column (Amersham-Pharmacia). GPC was performed at 4° C. in buffer A at a flow rate of 0.4 mL/min, and 1 mL fractions were collected. Fractions containing SHE activity were pooled and concentrated using an Amicon centricon microspin column (Millipore) to 500 μL. A second GPC purification was performed by application of 100 μL of the concentrated SHE-containing sample to a Superose 6 column (Amersham-Pharmacia). Superose 6 GPC was at 4° C. in buffer A with a flow rate of 0.2 mL/min, and 0.3 mL fractions were collected. Identification of the Superose 6 fractions containing SHE activity was achieved by starch zymogram analysis, which also provided the final step in the purification process, determination of the affinity of the purified protein for the starch substrate in the gel.

Purification of "conventional" alpha amylase from maize was achieved by the same methods as described for the purification of SHE. In this case, the alpha amylase activity was monitored at each step in the purification process enzymatically, using the Ceralpha kit (Megazyme). Briefly, this method assays the production of p-nitrophenol at 410 nm, which results from the hydrolysis of non-reducing ends that are blocked with p-nitrophenyl maltoheptaoside. Assays for "conventional" alpha amylase activity were conducted at 30° C. for 30 min and were terminated by the addition of 1% (w/v) Trizma base (Sigma).

Characterization of Purified Protein

The approximate molecular mass of SHE was determined by comparison of the elution of SHE from the analytical Superose 6 column to the elution of known MW standards from same column. Standard proteins used to calibrate the column were bovine thyroglobulin (670,000), bovine gamma globulin (158,000), chicken ovalbumin (44,000), horse myoglobin (17,000) and vitamin B-12 (1,350) (Bio-Rad).

Protein in pooled, concentrated Superose 6 fractions containing SHE activity was analyzed by SDS-PAGE on a 7% polyacrylamide gel, followed by staining of the gel with Coomassie brilliant blue and destaining with 50% methanol solution, according to standard procedures [29]. The approximate molecular mass of the strongly stained, abundant polypeptide corresponding to SHE was determined by comparison of the migration distance of the polypeptide with the migration of commercial molecular weight standards (Bio-Rad).

To identify the SHE protein in terms of its amino acid sequence, the band corresponding to SHE was excised from the SDS-polyacrylamide gel and analyzed by time-of-flight mass spectrometry (MALDI-TOF) according to standard methods [21]. At the mass spectrometry facility (Protein Facility, Iowa State University), the polypeptide was digested with the protease trypsin. The peptide fragments were concentrated, fractionated by capillary electrophoresis, and the eluent from the capillary was directly injected into the electrospray mass spectrometer, which separated the individual peptides. Computational algorithms utilized the differences between fragment masses to reveal the amino acid sequence of the original peptide, based on the expectation of fragmentation by cleavage of the peptide bonds. The peptide sequences were then compared to proteins in the public databases, enabling the sequence match of a peptide in a given gel band to a peptide within a protein sequence in the database.

Characterization of Hydrolysis Products

Purified SHE activity was analyzed by incubation of 20 µL of the pooled and concentrated Superose 6 fractions containing SHE activity with 100 µL of a 1% amylopectin (Sigma) or 1% beta limit-dextrin (Megazyme) solution. in a total volume of 200 µL. Incubation was at 37° C. for 24 h. Control incubations with both substrates also were conducted using "conventional" maize alpha amylase purified from developing maize endosperm, under the same conditions described for SHE incubation. Equivalent amounts of SHE and the alpha amylase control proteins were determined by quantification of the protein sample according to standard methods [3].

SHE amylopectin hydrolysis products were analyzed using a modified protocol for fluorophore-assisted carbohydrate electrophoresis (FACE) [7, 25]. Briefly, a 10 µL aliquot of the SHE amylopectin hydrolysis products was lyophilized, then resuspended in 30% DMSO and boiled for 10 min. A 10 µL aliquot was diluted to a final volume of 50 µL with 50 mM sodium acetate, pH 4.5. *Pseudomonas* sp. isoamylase (1 µL, 0.3 units) (Catalog No. E-ISAMY, Megazyme International, Bray, Ireland) was added and the reaction incubated overnight at 42° C. The mixture was heated in boiling water for 5 min and then centrifuged for 2 min at 12,000 g. A 10 µL sample of the reaction was evaporated to dryness in a Speed Vac. The reducing ends of the liberated oligosaccharide chains were derivatized with the fluorescent compound 8-amino-1,3,6-pyrenetrisulfonic acid (APTS) (Catalog No. 09341, Sigma-Aldrich, St. Louis, Mo.) by suspending the dried sample in 2 µL of 1 M sodium cyanoborohydride in tetrahydrafuran (Catalog No. 29,681-3, Sigma-Aldrich) and 2 µL APTS (0.1 mg/µL in 15% acetic acid). The reaction was incubated overnight at 42° C., diluted with 46 µL water, vortexed, and centrifuged briefly in a microfuge. A 5 µL aliquot was added to 195 µL purified water, and this sample was applied to a Beckman P/ACE capillary electrophoresis instrument. The sample injection parameters were 5 s at 0.5 psi. Separation was accomplished at 23.5 kV in an uncoated capillary using Carbohydrate Separation Gel Buffer N (Catalog Nos. 338451 and 477623, respectively, Beckman Coulter, Inc., Fullerton, Calif.).

SHE amylopectin and beta-limit dextrin hydrolysis products also were analyzed by GPC, using a Sephacryl CL-2B column (Amersham-Pharmacia; Ø=18 cm; H=50 cm) equilibrated with 10 mM NaOH. A 100 µL volume of the hydrolysis product was applied to the CL-2B column, and eluted at a flow rate of 12 mL/h in 1.4 mL fractions. Aliquots (30 µL) of each fraction were incubated with 50 µL amyloglucosidase solution (0.3 U in a 50 mM sodium citrate buffer, pH 4.6; Megazyme). The µg of glucose equivalents in each fraction was determined by the colorimetric glucose oxidase/peroxidase method (Sigma Diagnostics).

PCR Amplification, Cloning of ZmAmy3 cDNA and Nucleotide Sequence Analysis of the ZmAmy3 cDNA Total RNA was isolated from approximately 10 g *Zea mays* kernels (Oh43 inbred background) harvested 19 days after pollination, using a modification of the protocol reported by Chomczynski and Sacchi [6]. Briefly, frozen kernels were ground to a powder in liquid nitrogen, and RNA was extracted with Trizol reagent (Invitrogen). Addition of chloroform separated polysaccharides and DNA from the RNA-containing aqueous fraction. The RNA was then precipitated and air-dried, resuspended in water, and treated with DNase. The RNA was further purified using an RNeasy Plant Mini Kit (Qiagen).

Approximately 5 µg total RNA from developing maize kernels was reverse transcribed (RT) using a Superscript III First-Strand Synthesis System for RT-PCR kit (Invitrogen), using the oligo-(dT)18 primer provided. The RT product was used as the template for PCR amplification of a 2451 bp fragment of the ZmAmy3 cDNA. Five ZmAmy3 gene-specific primers were designed based on the sequence of an EST fragment in the maize genome (Genbank accession number PCO139185). These primers are designated KS052 (5'-GCC AAG TCT ATG AAG ACG CTT CC-3') (SEQ ID NO: 3), KS055 (5'-GCT GAT GGA GCA GGA AAC TC-3') (SEQ ID NO: 4), KS056 (5'-CTT CAG GCG ACA CAG AAT CA-3') (SEQ ID NO: 5), KS057 (5'-CTA CAA TCA GGA TGC CCA CA-3') (SEQ ID NO: 6), and KS058 (5'-AAC AAA GTT GAC AGC GGC GAT TGG A-3') (SEQ ID NO: 7). Degenerate primers were designed based on predicted orthologous sequences of the *Arabidopsis thaliana* Amy3 gene (Genbank accession number BT000643) and *Oryza sativa* Amy3 gene (Genbank accession number NM_191752). The degenerate primers are KS047 (5'-GGV AAR TGG GTS TTR CAT TGG GG-3') (SEQ ID NO: 8) and KS048 (5'-GGV AAR TGG GTS CTS CAT TGG GG-3') (SEQ ID NO: 9) (V=A, C or G; R=A or G; S=G or C). PCR amplification was conducted according to the protocol specified by the Accuzyme Pfx PCR Amplification kit (Invitrogen), using 500 ηg of the template DNA, and equivalent amounts (0.5 ηmol, final concentration) of primers KS052, KS047, and KS048. The complete nucleotide sequence of both strands of the amplified fragment was obtained using the three PCR primers as well as primers KS055, KS056, and KS057.

To obtain the 5' end of the ZmAmy3 cDNA, the rapid amplification of cDNA ends (RACE) [10] protocol was employed, using the GeneRacer kit (Invitrogen), according to instructions provided with the kit. Briefly, 5 µg RNA from maize kernels was reverse transcribed using the ZmAmy3-specific primer KS052 (0.5 ηmol, final concentration). PCR amplification of the 5' end was performed with Accuzyme Pfx polymerase, according to the kit protocol, using primer KS052 and a primer provided by the GeneRacer kit (5'-CGA CTG GAG CAC GAG GAC ACT GA-3') (SEQ ID NO: 10). The amplified DNA fragments were gel purified using the Qiaquick Gel Extraction kit (Qiagen). The purified PCR product was used as the template for a second-round PCR reaction using a nested ZmAmy3-specific primer KS059 (5'-GGG CTG TCC TTC TGA ATT GGG CAA A-3') (SEQ ID NO: 11) and a nested GeneRacer primer (5'-GGA CAC TGA CAT GGA CTG AAG GAG TA-3') (SEQ ID NO: 12). The amplified products were gel purified and sequenced using the same primers that were used for the amplification.

The PCR fragment containing the amplified ZmAmy3 cDNA was re-amplified for the purpose of cloning the fragment into a plasmid vector. Following a protocol based on the recombination-mediated cloning strategy of the Gateway Technology system (Invitrogen), two new PCR primers were used for the amplification: KS062 (5'-GGG GAC AAG TTT GTA CAA AAA AGC AGG CTG GGA AGT GGG TAC TGC ACT GGG G-3') (SEQ ID NO: 13), and KS063 (5'-GGG GAC CAC TTT GTA CAA GAA AGC TGG GTG CCA AGT CTA TGA AGA CGC TTC C-3') (SEQ ID NO: 14). The PCR product was gel purified and cloned into the Gateway cloning vector pDONR221 using the Invitrogen BP Clonase Enzyme Mix, according to the recommended protocol, generating plasmid pKS024. *E. coli* cells (DH-5α) were transformed with the plasmid DNA and screened for successful transformation events on LB media containing kanamycin. Plasmid DNA was isolated from successful transformants and the identity of pKS024 is confirmed by restriction enzyme analysis. Plasmid DNA was digested with both ApaI and HindIII, which produces fragments of 3738 and 1114 bp; BamHI, which produces fragments of 4449 and 553 bp; and with EcoRV and produces fragments of 2903 and 2100 bp.

The nucleotide sequence of plasmid pKS024 was determined by the chain termination method [30] using Sequenase Version 2.0 (U.S. Biochemical Corp.). The plasmid has been deposited with the American Type Culture Collection.

Deposits

Plasmid pKS024 was deposited on Sep. 24, 2004, with the American Type Culture Collection (ATCC), P.O. Box 1549, Manassas, Va. 20108 USA, as ATCC No. PTA-6235.

Applicants' assignee, Iowa State University Research Foundation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

REFERENCES

1. Beavis, W., Berlyn, M., Burr, B., Chandler, V., Coe, E., et al. 1995. A standard for maize genetics nomenclature. Maize Genet Coop Newsl 69: 182-184.
2. Beck, E. and Ziegler, P. 1989. Biosynthesis and degradation of starch in higher plants. Annu Rev Plant Physiol Plant Mol Biol 40: 95-117.
3. Bradford, M. M. 1976. A rapid and sensitive method for the quanitation of microgram quanitities of protein utilizing the principle of protein-dye binding. Analyt. Biochem. 72: 248-254.
4. Bradford, M. M. 1976. A rapid and sensitive method for the quantitation of microgram quantitities of protein utilizing the principle of protein-dye binding. Analyt. Biochem. 72: 248-254.
5. Cao, H., James, M. G. and Myers, A. M. 2000. Purification and characterization of soluble starch synthases from maize endosperm. Archives of Biochem and Biophys 373: 135-146.
6. Chomczynski, P. and Sacchi, N. 1987. Single-step method of RNA isolation by acid guanidinium thiocyanate-phenol-chloroform extraction. Anal Biochem 162: 156-159.
7. Dinges, J. R., Colleoni, C., Myers, A. M. and James, M. G. 2001. Molecular structure of three mutations at the maize sugaryl locus and their allele-specific phenotypic effects. Plant Physiol 125: 1406-1418.
8. Espigares, I., Elvira, C., Mano, J. F., Vazquez, B., San, R. J. and Reis, R. L. 2002. New partially degradable and bioactive acrylic bone cements based on starch blends and ceramic fillers. Biomaterials 23: 1883-1895.
9. French, D.: Organization of the starch granule. In: Whistler, R. L., BeMiller, J. M. and Paschall, E. F. (eds) Starch: Chemistry and technology, pp. 183-248. Academic Press, Orlando (1984).
10. Frohman, M., Dush, M. and Marlin, G. 1988. Rapid amplification of full-length cDNAs from rare transcripts: Amplification using a single gene-specific oligonucleotide primer. Proceedings of the National Academy of Sciences 85: 8998-9002.
11. Gallant, D. J., Bouchet, B. and Baldwin, P. M. 1997. Microscopy of starch: evidence of a new level of granule organization. Carbohydrate Polymers 32: 177-191.
12. Goff, S. A., Ricke, D., Lan, T. H., Presting, G., Wang, R., et al. 2002. A draft sequence of the rice genome (*Oryza sativa* L. ssp. *japonica*). Science 296: 92-100.
13. Guzman-Maldonado, H. and Paredes-Lopez, O. 1995. Amylolytic enzymes and products derived from starch: a review. Crit. Rev Food Sci Nutr 35: 373-403.
14. Huala, E., Dickerman, A. W., Garcia-Hernandez, M., Weems, D., Reiser, L., et al. 2001. The *Arabidopsis* Information Resource (TAIR): a comprehensive database and web-based information retrieval, analysis, and visualization system for a model plant. Nucleic Acids Res 29: 102-105.
15. Imberty, A., Buleon, A., Tran, V. and Perez, S. 1991. Recent advances in knowledge of starch structure. Starch/Staerke 43: 375-384.
16. Initiative, T. A. 2000. Analysis of the genome sequence of the flowering plant *Arabidopsis thaliana*. Nature 408: 796-815.
17. Jesperson, H. M., MacGregor, E. A., Henrissat, B., Sierks, M. R. and Svensson, B. 1993. Starch- and glycogen-debranching and branching enzymes: Prediction of structural features of the catalytic $(\beta/\alpha)_8$-barrel domain and evolutionary relationship to other amylolytic enzymes. J. Protein Chem. 12: 791-805.
18. Kennedy, J. F., Cabalda, V. M. and White, C. A. 1988. Enzymic starch utilization and genetic engineering. Trends in Biotechnology 6: 184-189.
19. MacGregor, E. A.: Structure and activity of some starch-metabolising enzymes. In: Park, K. H., Robyt, J. F. and Choi, Y.-D. (eds) Enzymes for Carbohydrate Engineering, pp. 109-124. Elsevier Science (1996).
20. MacGregor, E. A., Janecek, S, and Svensson, B. 2001. Relationship of sequence and structure to specificity in the alpha-amylase family of enzymes. Biochim Biophys Acta 1546: 1-20.
21. Mann, M., Hendrickson, R. C. and Pandey, A. 2001. Analysis of proteins and proteomes by mass spectrometry. Annu Rev Biochem 70: 437-473.
22. Marques, A. P., Reis, R. L. and Hunt, J. A. 2002. The biocompatibility of novel starch-based polymers and composites: in vitro studies. Biomaterials 23: 1471-1478.
23. Martin, C., Smith A. M. 1995. Starch biosynthesis. Plant Cell 7: 971-985.
24. Myers, A. M., Morell, M. K., James, M. G. and Ball, S. G. 2000. Recent progress toward understanding the amylopectin crystal. Plant Physiol 122.
25. O'Shea, M. G., Samuel, M. S., Konik, C. M. and Morell, M. K. 1998. Fluorophore-assisted carbohydrate electrophoresis (FACE) of oligosaccharides: efficiency of labelling and high-resolution separation. Carbohydr Res 307: 1-12.
26. Ritte, G., Lorberth, R. and Steup, M. 2000. Reversible binding of the starch-related R1 protein to the surface of transitory starch granules [In Process Citation]. Plant J 21: 387-391.
27. Robyt, J. F.: Enzymes in the hydrolysis and synthesis of starch. In: Whistler, R. L., BeMiller, J. M. and Paschall, E. F. (eds) Starch: Chemistry and technology, pp. 87-123. Academic Press, Orlando (1984).
28. Robyt, J. F.: Essentials of Carbohydrate Chemistry. Springer, New York (1998).

29. Sambrook, J., Fritsch, E. F. and Maniatis, T.: Molecular cloning. A laboratory manual. Cold Spring Harbor Laboratory, Cold Spring Harbor, N.Y. (1989).
30. Sanger, F., Nicklen, S, and Coulson, A. R. 1977. DNA sequencing with chain-terminating inhibitors. Proceedings of the National Academy of Sciences 74: 5463-5467.
31. Sogaard, M., Abe, J., Martin-Eauclaire, F. and Svensson, B. 1993. α-Amylases: structure and function. Carbohydrate Polymers 21: 137-146.
32. Svensson, B. 1994. Protein engineering in the alpha-amylase family: catalytic mechanism, substrate specificity, and stability. Plant Mol Biol 25: 141-157.
33. van Soest, J. J. and Vliegenthart, J. F. 1997. Crystallinity in starch plastics: consequences for material properties. Trends Biotechnol 15: 208-213.
34. Zeeman, S. C., Northrop, F., Smith, A. M. and Rees, T. 1998. A starch-accumulating mutant of *Arabidopsis thaliana* deficient in a chloroplastic starch-hydrolysing enzyme. Plant J 15: 357-365.
35. Zeeman, S. C., Umemoto, T., Lue, W. L., Au-Yeung, P., Martin, C., Smith, A. M. and Chen, J. 1998. A mutant of *Arabidopsis* lacking a chloroplastic isoamylase accumulates both starch and phytoglycogen. Plant Cell 10: 1699-1712.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An isolated nucleic acid comprising a nucleotide sequence encoding the alpha-amylase having the amino acid sequence of SEQ ID NO:2.

2. An isolated nucleic acid comprising the complement of a nucleotide sequence encoding the alpha-amylase having the amino acid sequence of SEQ ID NO:2.

3. An isolated nucleic acid comprising the nucleotide sequence of SEQ ID NO:1.

4. An isolated nucleic acid consisting of the nucleotide sequence of SEQ ID NO:1.

5. An isolated nucleic acid comprising the complement of the nucleotide sequence of SEQ ID NO:1.

6. An isolated nucleic acid consisting of the nucleotide sequence of the complement of SEQ ID NO:1.

7. A transgenic plant comprising a genome including a heterologous DNA sequence comprising a sequence encoding the alpha-amylase comprising the amino acid sequence of SEQ ID NO:2.

8. A transgenic plant comprising a genome including a heterologous DNA sequence encoding the alpha-amylase consisting of the amino acid sequence of SEQ ID NO:2.

9. A transgenic plant comprising a genome including a heterologous DNA sequence comprising the complement of a sequence encoding the alpha-amylase comprising the amino acid sequence of SEQ ID NO:2.

10. A transgenic plant comprising a genome including a heterologous DNA sequence consisting of the complement of the DNA sequence encoding the alpha-amylase consisting of the amino acid sequence of SEQ ID NO:2.

11. A recombinant expression vector comprising the isolated nucleic acid of claim 1.

12. A composition comprising a cell transformed with the recombinant expression vector of claim 11.

13. A recombinant expression vector comprising the isolated nucleic acid of claim 2.

14. A composition comprising a cell transformed with the recombinant expression vector of claim 13.

* * * * *

SEQUENCE LISTING

```
<160> NUMBER OF SEQ ID NOS: 16

<210> SEQ ID NO 1
<211> LENGTH: 2980
<212> TYPE: DNA
<213> ORGANISM: Zea maize
<220> FEATURE:
<221> NAME/KEY: CDS
<222> LOCATION: (1)...(2640)
<221> NAME/KEY: misc_feature
<222> LOCATION: 4, 6, 45, 81, 86, 87, 88
<223> OTHER INFORMATION: n = A,T,C or G

<400> SEQUENCE: 1 atg nan aaa tct tct ctc tct ctc tcc cgc tct att ttt ctc atn cgc        48
Met Xaa Lys Ser Ser Leu Ser Leu Ser Arg Ser Ile Phe Leu Xaa Arg
1               5                   10                  15 ttc ggc tcc ctc aca cac tca cac gca cac acn aga gnn ncg cac aca        96
Phe Gly Ser Leu Thr His Ser His Ala His Thr Arg Xaa Xaa His Thr
                20                  25                  30 ccc gct ctc tca gag aga gag aga gag aga gct agc cat gtc ggt ggg       144
Pro Ala Leu Ser Glu Arg Glu Arg Glu Arg Ala Ser His Val Gly Gly
            35                  40                  45 gag ttg ttg cat tcg tgc tat ccc ggg gcc gcg gag agc gcg gtg gct       192
Glu Leu Leu His Ser Cys Tyr Pro Gly Ala Ala Glu Ser Ala Val Ala
        50                  55                  60 ggc act gac gag gac gct gga gcg gcg ttc tcc gag acg ttc ccc ctg       240
Gly Thr Asp Glu Asp Ala Gly Ala Ala Phe Ser Glu Thr Phe Pro Leu
65                  70                  75                  80 cgc cga tgc caa gct gtg gaa ggg aag gcg tgg gtg agg gtg gac gca       288
Arg Arg Cys Gln Ala Val Glu Gly Lys Ala Trp Val Arg Val Asp Ala
                85                  90                  95 gag ccg gac tcc gaa ggc aag tgc aag gtc gtt gtt ggg tgt aat gtg       336
Glu Pro Asp Ser Glu Gly Lys Cys Lys Val Val Val Gly Cys Asn Val
            100                 105                 110 gcg ggg aag tgg gta ctg cac tgg ggt gtc tcg tac gat gat gaa cat       384
Ala Gly Lys Trp Val Leu His Trp Gly Val Ser Tyr Asp Asp Glu His
        115                 120                 125 gga aga gaa tgg gat cag cct cct tca gaa atg aga cca cct ggt tca       432
Gly Arg Glu Trp Asp Gln Pro Pro Ser Glu Met Arg Pro Pro Gly Ser
    130                 135                 140 gtt gca atc aag gac tat gca att gaa aca cca ttg gag att ttg ccc       480
Val Ala Ile Lys Asp Tyr Ala Ile Glu Thr Pro Leu Glu Ile Leu Pro
```

-continued

```
                145                 150                 155                 160
aat tca gaa gga cag ccc ctt tat gaa atg caa atc aaa ttt gat aaa      528
Asn Ser Glu Gly Gln Pro Leu Tyr Glu Met Gln Ile Lys Phe Asp Lys
                165                 170                 175 gac att cca atc gcc gct gtc aac ttt gtt cta aag gaa gag gaa aca      576
Asp Ile Pro Ile Ala Ala Val Asn Phe Val Leu Lys Glu Glu Glu Thr
                180                 185                 190 ggt gca tgg ttt cag cat aag ggc agg gat ttc aga ata ccc tta aat      624
Gly Ala Trp Phe Gln His Lys Gly Arg Asp Phe Arg Ile Pro Leu Asn
            195                 200                 205 gga tcc ttc aat gat ggc gga aaa caa gat att gat atc tgg cca gga      672
Gly Ser Phe Asn Asp Gly Gly Lys Gln Asp Ile Asp Ile Trp Pro Gly
        210                 215                 220 gat ttg ggg cat gta ttg aag aaa tct gaa ggc tct agt tct cag cca      720
Asp Leu Gly His Val Leu Lys Lys Ser Glu Gly Ser Ser Ser Gln Pro
225                 230                 235                 240 caa aac act tca cct gag gat aca ggt ttg agt ggc aaa cat ata tca      768
Gln Asn Thr Ser Pro Glu Asp Thr Gly Leu Ser Gly Lys His Ile Ser
                245                 250                 255 ggg ttc tat gag gaa tac ccc atc ctt aaa tca gag tat gtt cag aat      816
Gly Phe Tyr Glu Glu Tyr Pro Ile Leu Lys Ser Glu Tyr Val Gln Asn
                260                 265                 270 ctt gtt act gtc act gtg agg aga gac att gaa gcg cat aaa aga ctt      864
Leu Val Thr Val Thr Val Arg Arg Asp Ile Glu Ala His Lys Arg Leu
            275                 280                 285 gtg gaa ttt gac act gat att cct gga gaa gtt atc att cat tgg gga      912
Val Glu Phe Asp Thr Asp Ile Pro Gly Glu Val Ile Ile His Trp Gly
        290                 295                 300 gtt tgc aga gac aat act atg aca tgg gag atc cca cca gaa cca cat      960
Val Cys Arg Asp Asn Thr Met Thr Trp Glu Ile Pro Pro Glu Pro His
305                 310                 315                 320 cca cca aaa acg aaa ata ttc cga cac aaa gct ctt caa act ttg ctg     1008
Pro Pro Lys Thr Lys Ile Phe Arg His Lys Ala Leu Gln Thr Leu Leu
                325                 330                 335 cag caa aaa gct gat gga gca gga aac tca att tca ttc tca ctt gat     1056
Gln Gln Lys Ala Asp Gly Ala Gly Asn Ser Ile Ser Phe Ser Leu Asp
                340                 345                 350 gca gag tat tct tgt ctg ttt ttt gtg ctc aaa ctt gac gag tat act     1104
Ala Glu Tyr Ser Cys Leu Phe Phe Val Leu Lys Leu Asp Glu Tyr Thr
            355                 360                 365 tgg ttg aga aat ctt gag aat gga tct gat ttc tat gtg cca ctt aca     1152
Trp Leu Arg Asn Leu Glu Asn Gly Ser Asp Phe Tyr Val Pro Leu Thr
        370                 375                 380 aga gtg ggg cag tat ggc agc act cag gat cct gac aag gct gag gca     1200
Arg Val Gly Gln Tyr Gly Ser Thr Gln Asp Pro Asp Lys Ala Glu Ala
385                 390                 395                 400 cag aaa ata gag gat aag tct tca cag gct gat ggc tta atc agt gat     1248
Gln Lys Ile Glu Asp Lys Ser Ser Gln Ala Asp Gly Leu Ile Ser Asp
                405                 410                 415 ata aga aat ctg gtg gtt ggc cta tcg tct aga aga ggt cag aaa gct     1296
Ile Arg Asn Leu Val Val Gly Leu Ser Ser Arg Arg Gly Gln Lys Ala
                420                 425                 430 aag aat aaa gtt ctt caa gag gac atc cta caa gaa atc gaa aga ctt     1344
Lys Asn Lys Val Leu Gln Glu Asp Ile Leu Gln Glu Ile Glu Arg Leu
            435                 440                 445 gca gca gaa gct tat agc att ttc agg agc ccc act att gat tcc gta     1392
Ala Ala Glu Ala Tyr Ser Ile Phe Arg Ser Pro Thr Ile Asp Ser Val
        450                 455                 460 gat gaa tct gta cag ctc gat gac aca tta agc gca aag cca gca tgt     1440
```

-continued

| | | |
|---|---|---|
| Asp Glu Ser Val Gln Leu Asp Asp Thr Leu Ser Ala Lys Pro Ala Cys<br>465                    470                    475                    480 | |

```
tct ggc act gga tct ggt ttt gag ata ttg tgc caa gga ttt aac tgg       1488
Ser Gly Thr Gly Ser Gly Phe Glu Ile Leu Cys Gln Gly Phe Asn Trp
                485                 490                 495 gaa tct cat aaa tca ggg aaa tgg tat gtt gag ctt ggc aca aag gcc       1536
Glu Ser His Lys Ser Gly Lys Trp Tyr Val Glu Leu Gly Thr Lys Ala
        500                 505                 510 aag gag ttg tcg tcc ttg ggt ttc acc att gtc tgg tca cca cca cca       1584
Lys Glu Leu Ser Ser Leu Gly Phe Thr Ile Val Trp Ser Pro Pro Pro
    515                 520                 525 act gat tct gtg tca cct gaa gga tac atg cca agg gat cta tat aat       1632
Thr Asp Ser Val Ser Pro Glu Gly Tyr Met Pro Arg Asp Leu Tyr Asn
530                 535                 540 cta aac tca cga tat ggg tcc atg gat gag ctg aag gaa ctt gtg aag       1680
Leu Asn Ser Arg Tyr Gly Ser Met Asp Glu Leu Lys Glu Leu Val Lys
545                 550                 555                 560 att ttc cat gaa gct ggt atc aag gtt ctt ggc gac gct gtt cta aat       1728
Ile Phe His Glu Ala Gly Ile Lys Val Leu Gly Asp Ala Val Leu Asn
                565                 570                 575 cat agg tgt gct cag ttt cag aac aac aat ggt gtc tgg aat ata ttt       1776
His Arg Cys Ala Gln Phe Gln Asn Asn Asn Gly Val Trp Asn Ile Phe
        580                 585                 590 ggt ggt cgt atg aac tgg gat gat cga gca gtt gtt gct gat gat cca       1824
Gly Gly Arg Met Asn Trp Asp Asp Arg Ala Val Val Ala Asp Asp Pro
    595                 600                 605 cat ttc cag gga aga gga aac aag agc agt gga gat aat ttc cat gca       1872
His Phe Gln Gly Arg Gly Asn Lys Ser Ser Gly Asp Asn Phe His Ala
610                 615                 620 gca cca aac att gat cac tcc caa gag ttt gtg agg aat gat ctt aaa       1920
Ala Pro Asn Ile Asp His Ser Gln Glu Phe Val Arg Asn Asp Leu Lys
625                 630                 635                 640 gaa tgg ctt tgc tgg atg aga aag gaa gtc ggc tac gat gga tgg aga       1968
Glu Trp Leu Cys Trp Met Arg Lys Glu Val Gly Tyr Asp Gly Trp Arg
                645                 650                 655 ctt gac ttt gtt cgt ggt ttc tgg ggt gga tat gtc aag gac tat ttg       2016
Leu Asp Phe Val Arg Gly Phe Trp Gly Gly Tyr Val Lys Asp Tyr Leu
        660                 665                 670 gaa gca agt gaa cca tac ttt gca gta gga gag tac tgg gac tcc ctc       2064
Glu Ala Ser Glu Pro Tyr Phe Ala Val Gly Glu Tyr Trp Asp Ser Leu
    675                 680                 685 agt tat act tat ggt gaa atg gac tac aat cag gat gcc cac agg cag       2112
Ser Tyr Thr Tyr Gly Glu Met Asp Tyr Asn Gln Asp Ala His Arg Gln
690                 695                 700 aga att gtt gat tgg ata aat gct aca aat gga act gct ggc gca ttt       2160
Arg Ile Val Asp Trp Ile Asn Ala Thr Asn Gly Thr Ala Gly Ala Phe
705                 710                 715                 720 gat gtt acc act aaa gga ata ctt cat gcg gcg ctt gaa aga tca gag       2208
Asp Val Thr Thr Lys Gly Ile Leu His Ala Ala Leu Glu Arg Ser Glu
                725                 730                 735 tat tgg cgc ctg tcc gat gaa aaa ggg aaa ccc cct gga gta ttg ggt       2256
Tyr Trp Arg Leu Ser Asp Glu Lys Gly Lys Pro Pro Gly Val Leu Gly
        740                 745                 750 tgg tgg cct tca aga gca gtc aca ttt ata gag aat cat gat act ggt       2304
Trp Trp Pro Ser Arg Ala Val Thr Phe Ile Glu Asn His Asp Thr Gly
    755                 760                 765 tct act cag ggc cat tgg agg ttc ccc tat ggt atg gaa ctg caa gga       2352
Ser Thr Gln Gly His Trp Arg Phe Pro Tyr Gly Met Glu Leu Gln Gly
770                 775                 780
```

| | | | | | | | | | | | | | | | |
|---|---|---|---|---|---|---|---|---|---|---|---|---|---|---|---|
| tac | gcc | tac | atc | ctg | aca | cac | cct | ggc | act | ccc | gca | gtc | ttc | tat | gac | 2400 |
| Tyr | Ala | Tyr | Ile | Leu | Thr | His | Pro | Gly | Thr | Pro | Ala | Val | Phe | Tyr | Asp |
| 785 | | | | 790 | | | | | 795 | | | | | 800 | |

| | | | | | | | | | | | | | | | |
|---|---|---|---|---|---|---|---|---|---|---|---|---|---|---|---|
| cac | ata | ttt | tca | cac | tta | caa | cca | gag | atc | gct | aaa | ttt | att | tcc | att | 2448 |
| His | Ile | Phe | Ser | His | Leu | Gln | Pro | Glu | Ile | Ala | Lys | Phe | Ile | Ser | Ile |
| | | | | 805 | | | | | 810 | | | | | 815 | |

| cga | cac | cgt | caa | aag | att | cat | tgc | cgc | agc | aag | atc | aag | ata | cta | aag | 2496 |
|---|---|---|---|---|---|---|---|---|---|---|---|---|---|---|---|---|
| Arg | His | Arg | Gln | Lys | Ile | His | Cys | Arg | Ser | Lys | Ile | Lys | Ile | Leu | Lys |
| | | | 820 | | | | | 825 | | | | | 830 | | |

| gca | gag | agg | agt | tta | tat | gcg | gct | gaa | att | gat | gag | aag | gta | aca | atg | 2544 |
|---|---|---|---|---|---|---|---|---|---|---|---|---|---|---|---|---|
| Ala | Glu | Arg | Ser | Leu | Tyr | Ala | Ala | Glu | Ile | Asp | Glu | Lys | Val | Thr | Met |
| | | | | 835 | | | | | 840 | | | | | 845 | |

| aaa | atc | gga | tca | gaa | cat | ttt | gag | cca | agc | ggt | ccc | cag | aac | tgg | att | 2592 |
|---|---|---|---|---|---|---|---|---|---|---|---|---|---|---|---|---|
| Lys | Ile | Gly | Ser | Glu | His | Phe | Glu | Pro | Ser | Gly | Pro | Gln | Asn | Trp | Ile |
| 850 | | | | | 855 | | | | | 860 | | | | | |

| gtt | gct | gct | gag | ggt | caa | gat | tac | aaa | atc | tgg | gaa | gcg | tct | tca | tag | 2640 |
|---|---|---|---|---|---|---|---|---|---|---|---|---|---|---|---|---|
| Val | Ala | Ala | Glu | Gly | Gln | Asp | Tyr | Lys | Ile | Trp | Glu | Ala | Ser | Ser | * |
| 865 | | | | 870 | | | | | 875 | | | | | | |

| | |
|---|---|
| acttggcggg ctgcgagtgc catataactg ctcaaagact aaaaggaag ctacaagaaa | 2700 |
| gcataatgct aggagatggc gcctcagaat ggtcagctgg cgggagctgc tgccgctgcc | 2760 |
| gccatggagc agcaaaattc aacaacataa gctatggaag cacttgccac ggcgatagga | 2820 |
| ttatctaata ggactactgt tgaacattcg atatatccag aaccaccat catttgcagg | 2880 |
| cacattggcc attaaaattt agcttcgtcc tctattttgg agctatgtaa aagcatgcac | 2940 |
| aactctattt atgtgtgaaa taaaatttga aaacgcgtgg | 2980 |

<210> SEQ ID NO 2
<211> LENGTH: 879
<212> TYPE: PRT
<213> ORGANISM: Zea maize
<220> FEATURE:
<221> NAME/KEY: VARIANT
<222> LOCATION: 2, 15, 29, 30
<223> OTHER INFORMATION: Xaa = Any Amino Acid

<400> SEQUENCE: 2

Met Xaa Lys Ser Ser Leu Ser Leu Ser Arg Ser Ile Phe Leu Xaa Arg
1               5                   10                  15

Phe Gly Ser Leu Thr His Ser His Ala His Thr Arg Xaa Xaa His Thr
            20                  25                  30

Pro Ala Leu Ser Glu Arg Glu Arg Ala Ser His Val Gly Gly
        35                  40                  45

Glu Leu Leu His Ser Cys Tyr Pro Gly Ala Ala Glu Ser Ala Val Ala
    50                  55                  60

Gly Thr Asp Glu Asp Ala Gly Ala Ala Phe Ser Glu Thr Phe Pro Leu
65                  70                  75                  80

Arg Arg Cys Gln Ala Val Glu Gly Lys Ala Trp Val Arg Val Asp Ala
            85                  90                  95

Glu Pro Asp Ser Glu Gly Lys Cys Lys Val Val Gly Cys Asn Val
        100                 105                 110

Ala Gly Lys Trp Val Leu His Trp Gly Val Ser Tyr Asp Asp Glu His
    115                 120                 125

Gly Arg Glu Trp Asp Gln Pro Ser Glu Met Arg Pro Pro Gly Ser
130                 135                 140

Val Ala Ile Lys Asp Tyr Ala Ile Glu Thr Pro Leu Glu Ile Leu Pro
145                 150                 155                 160

Asn Ser Glu Gly Gln Pro Leu Tyr Glu Met Gln Ile Lys Phe Asp Lys

-continued

```
                165                 170                 175
Asp Ile Pro Ile Ala Ala Val Asn Phe Val Leu Lys Glu Glu Thr
            180                 185                 190
Gly Ala Trp Phe Gln His Lys Gly Arg Asp Phe Arg Ile Pro Leu Asn
            195                 200                 205
Gly Ser Phe Asn Asp Gly Lys Gln Asp Ile Asp Ile Trp Pro Gly
            210                 215                 220
Asp Leu Gly His Val Leu Lys Lys Ser Glu Gly Ser Ser Gln Pro
225                 230                 235                 240
Gln Asn Thr Ser Pro Glu Asp Thr Gly Leu Ser Gly Lys His Ile Ser
            245                 250                 255
Gly Phe Tyr Glu Glu Tyr Pro Ile Leu Lys Ser Glu Tyr Val Gln Asn
            260                 265                 270
Leu Val Thr Val Thr Val Arg Arg Asp Ile Glu Ala His Lys Arg Leu
            275                 280                 285
Val Glu Phe Asp Thr Asp Ile Pro Gly Glu Val Ile Ile His Trp Gly
            290                 295                 300
Val Cys Arg Asp Asn Thr Met Thr Trp Glu Ile Pro Pro Glu Pro His
305                 310                 315                 320
Pro Pro Lys Thr Lys Ile Phe Arg His Lys Ala Leu Gln Thr Leu Leu
            325                 330                 335
Gln Gln Lys Ala Asp Gly Ala Gly Asn Ser Ile Ser Phe Ser Leu Asp
            340                 345                 350
Ala Glu Tyr Ser Cys Leu Phe Phe Val Leu Lys Leu Asp Glu Tyr Thr
            355                 360                 365
Trp Leu Arg Asn Leu Glu Asn Gly Ser Asp Phe Tyr Val Pro Leu Thr
            370                 375                 380
Arg Val Gly Gln Tyr Gly Ser Thr Gln Asp Pro Asp Lys Ala Glu Ala
385                 390                 395                 400
Gln Lys Ile Glu Asp Lys Ser Ser Gln Ala Asp Gly Leu Ile Ser Asp
            405                 410                 415
Ile Arg Asn Leu Val Val Gly Leu Ser Ser Arg Arg Gly Gln Lys Ala
            420                 425                 430
Lys Asn Lys Val Leu Gln Glu Asp Ile Leu Gln Glu Ile Glu Arg Leu
            435                 440                 445
Ala Ala Glu Ala Tyr Ser Ile Phe Arg Ser Pro Thr Ile Asp Ser Val
            450                 455                 460
Asp Glu Ser Val Gln Leu Asp Asp Thr Leu Ser Ala Lys Pro Ala Cys
465                 470                 475                 480
Ser Gly Thr Gly Ser Gly Phe Glu Ile Leu Cys Gln Gly Phe Asn Trp
            485                 490                 495
Glu Ser His Lys Ser Gly Lys Trp Tyr Val Glu Leu Gly Thr Lys Ala
            500                 505                 510
Lys Glu Leu Ser Ser Leu Gly Phe Thr Ile Val Trp Ser Pro Pro
            515                 520                 525
Thr Asp Ser Val Ser Pro Glu Gly Tyr Met Pro Arg Asp Leu Tyr Asn
            530                 535                 540
Leu Asn Ser Arg Tyr Gly Ser Met Asp Glu Leu Lys Glu Leu Val Lys
545                 550                 555                 560
Ile Phe His Glu Ala Gly Ile Lys Val Leu Gly Asp Ala Val Leu Asn
            565                 570                 575
His Arg Cys Ala Gln Phe Gln Asn Asn Asn Gly Val Trp Asn Ile Phe
            580                 585                 590
```

-continued

```
Gly Gly Arg Met Asn Trp Asp Asp Arg Ala Val Val Ala Asp Asp Pro
            595                 600                 605

His Phe Gln Gly Arg Gly Asn Lys Ser Ser Gly Asp Asn Phe His Ala
        610                 615                 620

Ala Pro Asn Ile Asp His Ser Gln Glu Phe Val Arg Asn Asp Leu Lys
625                 630                 635                 640

Glu Trp Leu Cys Trp Met Arg Lys Glu Val Gly Tyr Asp Gly Trp Arg
            645                 650                 655

Leu Asp Phe Val Arg Gly Phe Trp Gly Gly Tyr Val Lys Asp Tyr Leu
        660                 665                 670

Glu Ala Ser Glu Pro Tyr Phe Ala Val Gly Glu Tyr Trp Asp Ser Leu
    675                 680                 685

Ser Tyr Thr Tyr Gly Glu Met Asp Tyr Asn Gln Asp Ala His Arg Gln
        690                 695                 700

Arg Ile Val Asp Trp Ile Asn Ala Thr Asn Gly Thr Ala Gly Ala Phe
705                 710                 715                 720

Asp Val Thr Thr Lys Gly Ile Leu His Ala Ala Leu Glu Arg Ser Glu
            725                 730                 735

Tyr Trp Arg Leu Ser Asp Glu Lys Gly Lys Pro Pro Gly Val Leu Gly
        740                 745                 750

Trp Trp Pro Ser Arg Ala Val Thr Phe Ile Glu Asn His Asp Thr Gly
    755                 760                 765

Ser Thr Gln Gly His Trp Arg Phe Pro Tyr Gly Met Glu Leu Gln Gly
        770                 775                 780

Tyr Ala Tyr Ile Leu Thr His Pro Gly Thr Pro Ala Val Phe Tyr Asp
785                 790                 795                 800

His Ile Phe Ser His Leu Gln Pro Glu Ile Ala Lys Phe Ile Ser Ile
            805                 810                 815

Arg His Arg Gln Lys Ile His Cys Arg Ser Lys Ile Lys Ile Leu Lys
        820                 825                 830

Ala Glu Arg Ser Leu Tyr Ala Ala Glu Ile Asp Glu Lys Val Thr Met
    835                 840                 845

Lys Ile Gly Ser Glu His Phe Glu Pro Ser Gly Pro Gln Asn Trp Ile
        850                 855                 860

Val Ala Ala Glu Gly Gln Asp Tyr Lys Ile Trp Glu Ala Ser Ser
865                 870                 875

<210> SEQ ID NO 3
<211> LENGTH: 23
<212> TYPE: DNA
<213> ORGANISM: Artificial Sequence
<220> FEATURE:
<223> OTHER INFORMATION: PCR Primer

<400> SEQUENCE: 3
gccaagtcta tgaagacgct tcc                                        23

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
gctgatggag caggaaactc                                            20
```

```
<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
cttcaggcga cacagaatca                                              20

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
ctacaatcag gatgcccaca                                              20

<210> SEQ ID NO 7
<211> LENGTH: 25
<212> TYPE: DNA
<213> ORGANISM: Artificial Sequence
<220> FEATURE:
<223> OTHER INFORMATION: PCR Primer

<400> SEQUENCE: 7
aacaaagttg acagcggcga ttgga                                        25

<210> SEQ ID NO 8
<211> LENGTH: 23
<212> TYPE: DNA
<213> ORGANISM: Artificial Sequence
<220> FEATURE:
<223> OTHER INFORMATION: PCR Primer

<400> SEQUENCE: 8
ggvaartggg tsttrcattg ggg                                          23

<210> SEQ ID NO 9
<211> LENGTH: 23
<212> TYPE: DNA
<213> ORGANISM: Artificial Sequence
<220> FEATURE:
<223> OTHER INFORMATION: PCR Primer

<400> SEQUENCE: 9
ggvaartggg tsctscattg ggg                                          23

<210> SEQ ID NO 10
<211> LENGTH: 23
<212> TYPE: DNA
<213> ORGANISM: Artificial Sequence
<220> FEATURE:
<223> OTHER INFORMATION: PCR Primer

<400> SEQUENCE: 10
cgactggagc acgaggacac tga                                          23

<210> SEQ ID NO 11
<211> LENGTH: 25
<212> TYPE: DNA
<213> ORGANISM: Artificial Sequence
<220> FEATURE:
<223> OTHER INFORMATION: PCR Primer
```

<400> SEQUENCE: 11
gggctgtcct tctgaattgg gcaaa                                              25

<210> SEQ ID NO 12
<211> LENGTH: 26
<212> TYPE: DNA
<213> ORGANISM: Artificial Sequence
<220> FEATURE:
<223> OTHER INFORMATION: PCR Primer

<400> SEQUENCE: 12
ggacactgac atggactgaa ggagta                                             26

<210> SEQ ID NO 13
<211> LENGTH: 52
<212> TYPE: DNA
<213> ORGANISM: Artificial Sequence
<220> FEATURE:
<223> OTHER INFORMATION: PCR Primer

<400> SEQUENCE: 13
ggggacaagt ttgtacaaaa aagcaggctg ggaagtgggt actgcactgg gg                52

<210> SEQ ID NO 14
<211> LENGTH: 51
<212> TYPE: DNA
<213> ORGANISM: Artificial Sequence
<220> FEATURE:
<223> OTHER INFORMATION: PCR Primer

<400> SEQUENCE: 14
ggggaccact ttgtacaaga aagctgggtg ccaagtctat gaagacgctt c                 51

<210> SEQ ID NO 15
<211> LENGTH: 906
<212> TYPE: PRT
<213> ORGANISM: Oryza sativa

<400> SEQUENCE: 15

Met Ala Val Ala Ser Trp Ser Ile Pro Ala Ile Pro Arg Ala Gly Pro
1               5                   10                  15

Thr Ala Arg Gly Val Leu Leu Gly Gly Ala Phe Val Thr Ala Ala Arg
            20                  25                  30

Pro Pro Val Ala Trp Arg Cys Arg Ala Thr Leu Pro Arg Arg Val Arg
        35                  40                  45

Leu Gly Gly Val Val Ala Arg Ala Gly Ala Ala Glu Thr Pro Val Ala
    50                  55                  60

Gly Ser Gly Glu Ala Gly Leu Leu Phe Ser Glu Lys Phe Pro Leu Arg
65                  70                  75                  80

Arg Ser Arg Thr Val Glu Gly Lys Ala Trp Val Arg Val Asp Ala Glu
                85                  90                  95

Pro Asp Gly Glu Gly Lys Cys Lys Val Val Ile Gly Cys Asp Val Glu
            100                 105                 110

Gly Lys Trp Val Leu His Trp Gly Val Ser Tyr Asp Gly Glu Gln Gly
        115                 120                 125

Arg Glu Trp Asp Gln Pro Pro Ser Asp Met Arg Pro Pro Gly Ser Val
    130                 135                 140

Pro Ile Lys Asp Tyr Ala Ile Glu Thr Ser Leu Asp Thr Pro His Asn
145                 150                 155                 160

```
Ser Glu Gly Lys Thr Ile His Glu Val Gln Ile Lys Ile Asp Lys Gly
                165                 170                 175

Thr Ser Ile Ala Ala Ile Asn Phe Val Leu Lys Val Gln Ile Leu Arg
            180                 185                 190

Cys Cys Ile Leu Tyr His Val Ser Lys Gly Leu Glu Val Tyr Asp Trp
                195                 200                 205

Pro Ile Arg Phe Val Lys Leu Leu Lys Val Pro Lys Glu Glu Glu Thr
210                 215                 220

Gly Ala Trp Phe Gln His Lys Gly Gln Asp Phe Arg Ile Pro Leu Ser
225                 230                 235                 240

Gly Ser Phe Gly Gly Asp Leu Leu Gly Thr Glu Gln Asp Ile Asp Val
                245                 250                 255

Arg Pro Gly His Leu Ser Asn Val Leu Gln Lys Pro Glu Gly Pro Ile
                260                 265                 270

Ala Glu Pro His Lys Thr Val Pro Asp Asp Lys Gly Ser Arg Thr Lys
                275                 280                 285

His Ile Ser Gly Phe Tyr Glu Glu Tyr Pro Ile Leu Lys Thr Val Tyr
                290                 295                 300

Val Gln Asn Phe Ile Thr Val Asn Val Arg Glu Asn Asn Gly Thr Thr
305                 310                 315                 320

Lys His Ala Val Glu Phe Asp Thr Asp Ile Pro Gly Glu Val Ile Ile
                325                 330                 335

His Trp Gly Val Cys Lys Asp Asn Thr Met Thr Trp Glu Ile Pro Pro
                340                 345                 350

Glu Pro His Pro Pro Ala Thr Lys Ile Phe Arg Gln Lys Ala Leu Gln
                355                 360                 365

Thr Met Leu Gln Gln Lys Ala Asp Gly Thr Gly Asn Ser Leu Ser Phe
                370                 375                 380

Leu Leu Asp Gly Glu Tyr Ser Gly Leu Ile Phe Val Val Lys Leu Asp
385                 390                 395                 400

Glu Tyr Thr Trp Leu Arg Asn Val Glu Asn Gly Phe Asp Phe Tyr Ile
                405                 410                 415

Pro Leu Thr Arg Ala Asp Ala Glu Ala Asp Lys Gln Lys Ala Asp Asp
                420                 425                 430

Lys Ser Ser Gln Asp Asp Gly Leu Ile Ser Asp Ile Arg Asn Leu Val
                435                 440                 445

Val Gly Leu Ser Ser Arg Arg Gly Gln Arg Ala Lys Asn Lys Val Leu
                450                 455                 460

Gln Glu Asp Ile Leu Gln Glu Ile Glu Arg Leu Ala Ala Glu Ala Tyr
465                 470                 475                 480

Ser Ile Phe Arg Ser Pro Thr Ile Asp Thr Val Glu Glu Ser Val Tyr
                485                 490                 495

Ile Asp Asp Ser Ser Ile Val Lys Pro Ala Cys Ser Gly Thr Gly Ser
                500                 505                 510

Gly Phe Glu Ile Leu Cys Gln Gly Phe Asn Trp Glu Ser His Lys Ser
                515                 520                 525

Gly Lys Trp Tyr Val Glu Leu Gly Ser Lys Ala Lys Glu Leu Ser Ser
                530                 535                 540

Met Gly Phe Thr Ile Val Trp Ser Pro Pro Thr Asp Ser Val Ser
545                 550                 555                 560

Pro Glu Gly Tyr Met Pro Arg Asp Leu Tyr Asn Leu Asn Ser Arg Tyr
                565                 570                 575

Gly Thr Met Glu Glu Leu Lys Glu Ala Val Lys Arg Phe His Glu Ala
```

```
                    580                 585                 590
Gly Met Lys Val Leu Gly Asp Ala Val Leu Asn His Arg Cys Ala Gln
                595                 600                 605

Phe Gln Asn Gln Asn Gly Val Trp Asn Ile Phe Gly Gly Arg Leu Asn
            610                 615                 620

Trp Asp Asp Arg Ala Val Ala Asp Pro His Phe Gln Gly Arg
625                 630                 635                 640

Gly Asn Lys Ser Ser Gly Asp Asn Phe His Ala Ala Pro Asn Ile Asp
                645                 650                 655

His Ser Gln Glu Phe Val Arg Ser Asp Leu Lys Glu Trp Leu Cys Trp
            660                 665                 670

Met Arg Lys Glu Val Gly Tyr Asp Gly Trp Arg Leu Asp Phe Val Arg
                675                 680                 685

Gly Phe Trp Gly Gly Tyr Val His Asp Tyr Leu Glu Ala Ser Glu Pro
            690                 695                 700

Tyr Phe Ala Val Gly Glu Tyr Trp Asp Ser Leu Ser Tyr Thr Tyr Gly
705                 710                 715                 720

Glu Met Asp Tyr Asn Gln Asp Ala His Arg Gln Arg Ile Val Asp Trp
                725                 730                 735

Ile Asn Ala Thr Asn Gly Thr Ala Gly Ala Phe Asp Val Thr Thr Lys
            740                 745                 750

Gly Ile Leu His Ser Ala Leu Glu Arg Ser Glu Tyr Trp Arg Leu Ser
                755                 760                 765

Asp Glu Lys Gly Lys Pro Pro Gly Val Leu Gly Trp Trp Pro Ser Arg
            770                 775                 780

Ala Val Thr Phe Ile Glu Asn His Asp Thr Gly Ser Thr Gln Gly His
785                 790                 795                 800

Trp Arg Phe Pro Phe Gly Met Glu Leu Gln Gly Tyr Val Tyr Ile Leu
                805                 810                 815

Thr His Pro Gly Thr Pro Ala Ile Phe Tyr Asp His Ile Phe Ser His
            820                 825                 830

Leu Gln Pro Glu Ile Ala Lys Leu Ile Ser Ile Arg Asn Arg Gln Lys
                835                 840                 845

Ile His Cys Arg Ser Lys Ile Lys Ile Leu Lys Ala Glu Gly Asn Leu
            850                 855                 860

Tyr Ala Ala Glu Ile Asp Glu Arg Val Thr Met Lys Ile Gly Ala Gly
865                 870                 875                 880

His Phe Glu Pro Ser Gly Pro Thr Asn Trp Val Val Ala Ala Glu Gly
                885                 890                 895

Gln Asp Tyr Lys Val Trp Glu Val Ser Ser
            900                 905

<210> SEQ ID NO 16
<211> LENGTH: 2980
<212> TYPE: PRT
<213> ORGANISM: Zea miaze

<400> SEQUENCE: 16

Ala Thr Gly Asn Ala Asn Ala Ala Ala Thr Cys Thr Cys Thr Cys
1               5                   10                  15

Thr Cys Thr Cys Thr Cys Thr Cys Thr Cys Cys Gly Cys Thr Cys
                20                  25                  30

Thr Ala Thr Thr Thr Thr Thr Cys Thr Cys Ala Thr Asn Cys Gly Cys
            35                  40                  45
```

-continued

```
Thr Thr Cys Gly Gly Cys Thr Cys Cys Cys Thr Cys Ala Cys Ala Cys
    50                  55                  60

Ala Cys Thr Cys Ala Cys Ala Cys Gly Cys Ala Cys Ala Cys Ala Cys
65                  70                  75                  80

Asn Ala Gly Ala Gly Asn Asn Asn Cys Gly Cys Ala Cys Ala Cys Ala
                85                  90                  95

Cys Cys Cys Gly Cys Thr Cys Thr Cys Thr Cys Ala Gly Ala Gly Ala
            100                 105                 110

Gly Ala Gly Ala Gly Ala Gly Ala Gly Ala Gly Ala Gly Ala Gly Cys
        115                 120                 125

Thr Ala Gly Cys Cys Ala Thr Gly Thr Cys Gly Gly Thr Gly Gly Gly
    130                 135                 140

Gly Ala Gly Thr Thr Gly Thr Thr Gly Cys Ala Thr Thr Cys Gly Thr
145                 150                 155                 160

Gly Cys Thr Ala Thr Cys Cys Cys Gly Gly Gly Gly Cys Cys Gly Cys
                165                 170                 175

Gly Gly Ala Gly Ala Gly Cys Gly Cys Gly Gly Thr Gly Gly Cys Thr
            180                 185                 190

Gly Gly Cys Ala Cys Thr Gly Ala Cys Gly Ala Gly Gly Ala Cys Gly
        195                 200                 205

Cys Thr Gly Gly Ala Gly Cys Gly Gly Cys Gly Thr Thr Cys Thr Cys
    210                 215                 220

Cys Gly Ala Gly Ala Cys Gly Thr Thr Cys Cys Cys Cys Cys Thr Gly
225                 230                 235                 240

Cys Gly Cys Cys Gly Ala Thr Gly Cys Cys Ala Ala Gly Cys Thr Gly
                245                 250                 255

Thr Gly Gly Ala Ala Gly Gly Gly Ala Ala Gly Gly Cys Gly Thr Gly
            260                 265                 270

Gly Gly Thr Gly Ala Gly Gly Gly Thr Gly Gly Ala Cys Gly Cys Ala
        275                 280                 285

Gly Ala Gly Cys Cys Gly Gly Ala Cys Thr Cys Cys Gly Ala Ala Gly
    290                 295                 300

Gly Cys Ala Ala Gly Thr Gly Cys Ala Ala Gly Gly Thr Cys Gly Thr
305                 310                 315                 320

Thr Gly Thr Thr Gly Gly Gly Thr Gly Thr Ala Ala Thr Gly Thr Gly
                325                 330                 335

Gly Cys Gly Gly Gly Gly Ala Ala Gly Thr Gly Gly Gly Thr Ala Cys
            340                 345                 350

Thr Gly Cys Ala Cys Thr Gly Gly Gly Gly Thr Gly Thr Cys Thr Cys
        355                 360                 365

Gly Thr Ala Cys Gly Ala Thr Gly Ala Thr Gly Ala Ala Cys Ala Thr
    370                 375                 380

Gly Gly Ala Ala Gly Ala Gly Ala Ala Thr Gly Gly Gly Ala Thr Cys
385                 390                 395                 400

Ala Gly Cys Cys Thr Cys Cys Thr Thr Cys Ala Gly Ala Ala Ala Thr
                405                 410                 415

Gly Ala Gly Ala Cys Cys Ala Cys Cys Thr Gly Gly Thr Thr Cys Ala
            420                 425                 430

Gly Thr Thr Gly Cys Ala Ala Thr Cys Ala Ala Gly Gly Ala Cys Thr
        435                 440                 445

Ala Thr Gly Cys Ala Ala Thr Thr Gly Ala Ala Ala Cys Ala Cys Cys
    450                 455                 460

Ala Thr Thr Gly Gly Ala Gly Ala Thr Thr Thr Thr Gly Cys Cys Cys
```

-continued

```
            465                 470                 475                 480
Ala Ala Thr Thr Cys Ala Gly Ala Gly Ala Cys Ala Gly Cys
                    485                 490                 495
Cys Cys Cys Thr Thr Thr Ala Thr Gly Ala Ala Thr Gly Cys Ala
                    500                 505                 510
Ala Ala Thr Cys Ala Ala Ala Thr Thr Gly Ala Thr Ala Ala Ala
                    515                 520                 525
Gly Ala Cys Ala Thr Thr Cys Cys Ala Ala Thr Cys Gly Cys Cys Gly
    530                 535                 540
Cys Thr Gly Thr Cys Ala Ala Cys Thr Thr Gly Thr Thr Cys Thr
545                 550                 555                 560
Ala Ala Ala Gly Gly Ala Ala Gly Ala Gly Gly Ala Ala Cys Ala
                    565                 570                 575
Gly Gly Thr Gly Cys Ala Thr Gly Gly Thr Thr Thr Cys Ala Gly Cys
                    580                 585                 590
Ala Thr Ala Ala Gly Gly Gly Cys Ala Gly Gly Ala Thr Thr Thr
                    595                 600                 605
Cys Ala Gly Ala Ala Thr Ala Cys Cys Thr Thr Ala Ala Ala Thr
                    610                 615                 620
Gly Gly Ala Thr Cys Cys Thr Thr Cys Ala Ala Thr Gly Ala Thr Gly
625                 630                 635                 640
Gly Cys Gly Gly Ala Ala Ala Cys Ala Ala Gly Ala Thr Ala Thr
                    645                 650                 655
Thr Gly Ala Thr Ala Thr Cys Thr Gly Gly Cys Cys Ala Gly Gly Ala
                    660                 665                 670
Gly Ala Thr Thr Thr Gly Gly Gly Cys Ala Thr Gly Thr Ala Thr
                    675                 680                 685
Thr Gly Ala Ala Gly Ala Ala Ala Thr Cys Thr Gly Ala Ala Gly Gly
                    690                 695                 700
Cys Thr Cys Thr Ala Gly Thr Thr Cys Thr Cys Ala Gly Cys Cys Ala
705                 710                 715                 720
Cys Ala Ala Ala Ala Cys Ala Cys Thr Thr Cys Ala Cys Cys Thr Gly
                    725                 730                 735
Ala Gly Gly Ala Thr Ala Cys Ala Gly Gly Thr Thr Thr Gly Ala Gly
                    740                 745                 750
Thr Gly Gly Cys Ala Ala Ala Cys Ala Thr Ala Thr Ala Thr Cys Ala
                    755                 760                 765
Gly Gly Gly Thr Thr Cys Thr Ala Thr Gly Ala Gly Gly Ala Ala Thr
                    770                 775                 780
Ala Cys Cys Cys Ala Thr Cys Cys Thr Thr Ala Ala Ala Thr Cys
785                 790                 795                 800
Ala Gly Ala Gly Thr Ala Thr Thr Thr Cys Ala Gly Ala Ala Thr
                    805                 810                 815
Cys Thr Thr Gly Thr Thr Ala Cys Thr Gly Thr Cys Ala Cys Thr Gly
                    820                 825                 830
Thr Gly Ala Gly Gly Ala Gly Ala Gly Ala Cys Ala Thr Thr Gly Ala
                    835                 840                 845
Ala Gly Cys Gly Cys Ala Thr Ala Ala Ala Gly Ala Cys Thr Thr
                    850                 855                 860
Gly Thr Gly Gly Ala Ala Thr Thr Gly Ala Cys Ala Cys Thr Gly
865                 870                 875                 880
Ala Thr Ala Thr Thr Cys Cys Thr Gly Gly Ala Gly Ala Ala Gly Thr
                    885                 890                 895
```

-continued

```
Thr Ala Thr Cys Ala Thr Thr Cys Ala Thr Thr Gly Gly Gly Gly Ala
            900                 905                 910

Gly Thr Thr Thr Gly Cys Ala Gly Ala Gly Ala Cys Ala Ala Thr Ala
        915                 920                 925

Cys Thr Ala Thr Gly Ala Cys Ala Thr Gly Gly Gly Ala Gly Ala Thr
    930                 935                 940

Cys Cys Cys Ala Cys Cys Ala Gly Ala Ala Cys Cys Ala Cys Ala Thr
945                 950                 955                 960

Cys Cys Ala Cys Cys Ala Ala Ala Ala Ala Cys Gly Ala Ala Ala Ala
                965                 970                 975

Thr Ala Thr Thr Cys Cys Gly Ala Cys Ala Cys Ala Ala Ala Gly Cys
            980                 985                 990

Thr Cys Thr Thr Cys Ala Ala Ala Cys Thr Thr Thr Gly Cys Thr Gly
        995                 1000                1005

Cys Ala Gly Cys Ala Ala Ala Ala Ala Gly Cys Thr Gly Ala Thr Gly
    1010                1015                1020

Gly Ala Gly Cys Ala Gly Gly Ala Ala Ala Cys Thr Cys Ala Ala Thr
1025                1030                1035                1040

Thr Thr Cys Ala Thr Thr Cys Thr Cys Ala Cys Thr Thr Gly Ala Thr
                1045                1050                1055

Gly Cys Ala Gly Ala Gly Thr Ala Thr Thr Cys Thr Thr Gly Thr Cys
            1060                1065                1070

Thr Gly Thr Thr Thr Thr Thr Thr Gly Thr Gly Cys Thr Cys Ala Ala
        1075                1080                1085

Ala Cys Thr Thr Gly Ala Cys Gly Ala Gly Thr Ala Thr Ala Cys Thr
    1090                1095                1100

Thr Gly Gly Thr Thr Gly Ala Gly Ala Ala Ala Thr Cys Thr Thr Gly
1105                1110                1115                1120

Ala Gly Ala Ala Thr Gly Gly Ala Thr Cys Thr Gly Ala Thr Thr Thr
                1125                1130                1135

Cys Thr Ala Thr Gly Thr Gly Cys Cys Ala Cys Thr Thr Ala Cys Ala
            1140                1145                1150

Ala Gly Ala Gly Thr Gly Gly Gly Gly Cys Ala Gly Thr Ala Thr Gly
        1155                1160                1165

Gly Cys Ala Gly Cys Ala Cys Thr Cys Ala Gly Gly Ala Thr Cys Cys
    1170                1175                1180

Thr Gly Ala Cys Ala Ala Gly Gly Cys Thr Gly Ala Gly Gly Cys Ala
1185                1190                1195                1200

Cys Ala Gly Ala Ala Ala Ala Thr Ala Gly Ala Gly Gly Ala Thr Ala
                1205                1210                1215

Ala Gly Thr Cys Thr Thr Cys Ala Cys Ala Gly Gly Cys Thr Gly Ala
            1220                1225                1230

Thr Gly Gly Cys Thr Thr Ala Ala Thr Cys Ala Gly Thr Gly Ala Thr
        1235                1240                1245

Ala Thr Ala Ala Gly Ala Ala Ala Thr Cys Thr Gly Gly Thr Gly Gly
    1250                1255                1260

Thr Thr Gly Gly Cys Cys Thr Ala Thr Cys Gly Thr Cys Thr Ala Gly
1265                1270                1275                1280

Ala Ala Gly Ala Gly Gly Thr Cys Ala Gly Ala Ala Ala Gly Cys Thr
                1285                1290                1295

Ala Ala Gly Ala Ala Thr Ala Ala Ala Gly Thr Thr Cys Thr Thr Cys
            1300                1305                1310
```

-continued

```
Ala Ala Gly Ala Gly Gly Ala Cys Ala Thr Cys Cys Thr Ala Cys Ala
        1315                1320                1325
Ala Gly Ala Ala Ala Thr Cys Gly Ala Ala Gly Ala Cys Thr Thr
        1330                1335                1340
Gly Cys Ala Gly Cys Ala Gly Ala Ala Gly Cys Thr Ala Thr Ala
1345                1350                1355                1360
Gly Cys Ala Thr Thr Thr Thr Cys Ala Gly Gly Ala Gly Cys Cys
        1365                1370                1375
Cys Ala Cys Thr Ala Thr Thr Gly Ala Thr Thr Cys Cys Gly Thr Ala
        1380                1385                1390
Gly Ala Thr Gly Ala Ala Thr Cys Thr Gly Thr Ala Cys Ala Gly Cys
        1395                1400                1405
Thr Cys Gly Ala Thr Gly Ala Cys Ala Cys Ala Thr Thr Ala Ala Gly
        1410                1415                1420
Cys Gly Cys Ala Ala Ala Gly Cys Cys Ala Gly Cys Ala Thr Gly Thr
1425                1430                1435                1440
Thr Cys Thr Gly Gly Cys Ala Cys Thr Gly Gly Ala Thr Cys Thr Gly
        1445                1450                1455
Gly Thr Thr Thr Thr Gly Ala Gly Ala Thr Ala Thr Thr Gly Thr Gly
        1460                1465                1470
Cys Cys Ala Ala Gly Gly Ala Thr Thr Ala Ala Cys Thr Gly Gly
        1475                1480                1485
Gly Ala Ala Thr Cys Thr Cys Ala Thr Ala Ala Ala Thr Cys Ala Gly
        1490                1495                1500
Gly Gly Ala Ala Ala Thr Gly Gly Thr Ala Thr Gly Thr Thr Gly Ala
1505                1510                1515                1520
Gly Cys Thr Thr Gly Gly Cys Ala Cys Ala Ala Ala Gly Gly Cys Cys
        1525                1530                1535
Ala Ala Gly Gly Ala Gly Thr Thr Gly Thr Cys Gly Thr Cys Cys Thr
        1540                1545                1550
Thr Gly Gly Gly Thr Thr Thr Cys Ala Cys Cys Ala Thr Thr Gly Thr
        1555                1560                1565
Cys Thr Gly Gly Thr Cys Ala Cys Cys Ala Cys Cys Ala Cys Cys Ala
        1570                1575                1580
Ala Cys Thr Gly Ala Thr Thr Cys Thr Gly Thr Cys Ala Cys
1585                1590                1595                1600
Cys Thr Gly Ala Ala Gly Gly Ala Thr Ala Cys Ala Thr Gly Cys Cys
        1605                1610                1615
Ala Ala Gly Gly Gly Ala Thr Cys Thr Ala Thr Ala Thr Ala Ala Thr
        1620                1625                1630
Cys Thr Ala Ala Ala Cys Thr Cys Ala Cys Gly Ala Thr Ala Thr Gly
        1635                1640                1645
Gly Gly Thr Cys Cys Ala Thr Gly Gly Ala Thr Gly Ala Gly Cys Thr
        1650                1655                1660
Gly Ala Ala Gly Gly Ala Ala Cys Thr Thr Gly Thr Gly Ala Ala Gly
1665                1670                1675                1680
Ala Thr Thr Thr Thr Cys Cys Ala Thr Gly Ala Ala Gly Cys Thr Gly
        1685                1690                1695
Gly Thr Ala Thr Cys Ala Ala Gly Gly Thr Thr Cys Thr Thr Gly Gly
        1700                1705                1710
Cys Gly Ala Cys Gly Cys Thr Gly Thr Thr Cys Thr Ala Ala Ala Thr
        1715                1720                1725
Cys Ala Thr Ala Gly Gly Thr Gly Thr Gly Cys Thr Cys Ala Gly Thr
```

-continued

```
                1730              1735              1740
Thr Thr Cys Ala Gly Ala Ala Cys Ala Ala Cys Ala Ala Thr Gly Gly
1745              1750              1755              1760
Thr Gly Thr Cys Thr Gly Gly Ala Ala Thr Ala Thr Ala Thr Thr Thr
                1765              1770              1775
Gly Gly Thr Gly Gly Thr Cys Gly Thr Ala Thr Gly Ala Ala Cys Thr
                1780              1785              1790
Gly Gly Gly Ala Thr Gly Ala Thr Cys Gly Ala Gly Cys Ala Gly Thr
                1795              1800              1805
Thr Gly Thr Thr Gly Cys Thr Gly Ala Thr Gly Ala Thr Cys Cys Ala
                1810              1815              1820
Cys Ala Thr Thr Cys Cys Ala Gly Gly Ala Ala Gly Ala Gly
1825              1830              1835              1840
Gly Ala Ala Ala Cys Ala Ala Gly Ala Gly Cys Ala Gly Thr Gly Gly
                1845              1850              1855
Ala Gly Ala Thr Ala Ala Thr Thr Cys Cys Ala Thr Gly Cys Ala
                1860              1865              1870
Gly Cys Ala Cys Cys Ala Ala Cys Ala Thr Thr Gly Ala Thr Cys
                1875              1880              1885
Ala Cys Thr Cys Cys Cys Ala Ala Gly Ala Gly Thr Thr Thr Gly Thr
                1890              1895              1900
Gly Ala Gly Gly Ala Ala Thr Gly Ala Thr Cys Thr Thr Ala Ala Ala
1905              1910              1915              1920
Gly Ala Ala Thr Gly Gly Cys Thr Thr Thr Gly Cys Thr Gly Gly Ala
                1925              1930              1935
Thr Gly Ala Gly Ala Ala Ala Gly Gly Ala Ala Gly Thr Cys Gly Gly
                1940              1945              1950
Cys Thr Ala Cys Gly Ala Thr Gly Gly Ala Thr Gly Gly Ala Gly Ala
                1955              1960              1965
Cys Thr Thr Gly Ala Cys Thr Thr Gly Thr Thr Cys Gly Thr Gly
                1970              1975              1980
Gly Thr Thr Thr Cys Thr Gly Gly Gly Gly Thr Gly Gly Ala Thr Ala
1985              1990              1995              2000
Thr Gly Thr Cys Ala Ala Gly Gly Ala Cys Thr Ala Thr Thr Gly
                2005              2010              2015
Gly Ala Ala Gly Cys Ala Ala Gly Thr Gly Ala Ala Cys Cys Ala Thr
                2020              2025              2030
Ala Cys Thr Thr Thr Gly Cys Ala Gly Thr Ala Gly Gly Ala Gly Ala
                2035              2040              2045
Gly Thr Ala Cys Thr Gly Gly Gly Ala Cys Thr Cys Cys Cys Thr Cys
                2050              2055              2060
Ala Gly Thr Thr Ala Thr Ala Cys Thr Thr Ala Thr Gly Gly Thr Gly
2065              2070              2075              2080
Ala Ala Ala Thr Gly Gly Ala Cys Thr Ala Cys Ala Ala Thr Cys Ala
                2085              2090              2095
Gly Gly Ala Thr Gly Cys Cys Ala Cys Ala Gly Gly Cys Ala Gly
                2100              2105              2110
Ala Gly Ala Ala Thr Thr Gly Thr Thr Gly Ala Thr Gly Gly Ala
                2115              2120              2125
Thr Ala Ala Ala Thr Gly Cys Thr Ala Cys Ala Ala Ala Thr Gly Gly
                2130              2135              2140
Ala Ala Cys Thr Gly Cys Thr Gly Gly Cys Gly Cys Ala Thr Thr Thr
2145              2150              2155              2160
```

```
Gly Ala Thr Gly Thr Thr Ala Cys Cys Ala Cys Thr Ala Ala Gly
            2165                2170                2175

Gly Ala Ala Thr Ala Cys Thr Thr Cys Ala Thr Gly Cys Gly Gly Cys
            2180                2185                2190

Gly Cys Thr Thr Gly Ala Ala Ala Gly Ala Thr Cys Ala Gly Ala Gly
            2195                2200                2205

Thr Ala Thr Thr Gly Gly Cys Gly Cys Thr Gly Thr Cys Cys Gly
            2210                2215                2220

Ala Thr Gly Ala Ala Ala Ala Gly Gly Ala Ala Cys Cys
2225                2230                2235                2240

Cys Cys Cys Thr Gly Gly Ala Gly Thr Ala Thr Thr Gly Gly Thr
            2245                2250                2255

Thr Gly Gly Thr Gly Gly Cys Cys Thr Thr Cys Ala Ala Gly Ala Gly
            2260                2265                2270

Cys Ala Gly Thr Cys Ala Cys Ala Thr Thr Ala Thr Ala Gly Ala
            2275                2280                2285

Gly Ala Ala Thr Cys Ala Thr Gly Ala Thr Ala Cys Thr Gly Gly Thr
            2290                2295                2300

Thr Cys Thr Ala Cys Thr Cys Ala Gly Gly Cys Cys Ala Thr Thr
2305                2310                2315                2320

Gly Gly Ala Gly Gly Thr Thr Cys Cys Cys Thr Ala Thr Gly Gly
            2325                2330                2335

Thr Ala Thr Gly Gly Ala Ala Cys Thr Gly Cys Ala Ala Gly Gly Ala
            2340                2345                2350

Thr Ala Cys Gly Cys Cys Thr Ala Cys Ala Thr Cys Thr Gly Ala
            2355                2360                2365

Cys Ala Cys Ala Cys Cys Thr Gly Gly Cys Ala Cys Thr Cys Cys
            2370                2375                2380

Cys Gly Cys Ala Gly Thr Cys Thr Thr Cys Thr Ala Thr Gly Ala Cys
2385                2390                2395                2400

Cys Ala Cys Ala Thr Ala Thr Thr Thr Cys Ala Cys Ala Cys Thr
            2405                2410                2415

Thr Ala Cys Ala Ala Cys Cys Ala Gly Ala Gly Ala Thr Cys Gly Cys
            2420                2425                2430

Thr Ala Ala Ala Thr Thr Thr Ala Thr Thr Cys Cys Ala Thr Thr
            2435                2440                2445

Cys Gly Ala Cys Ala Cys Cys Gly Thr Cys Ala Ala Ala Ala Gly Ala
            2450                2455                2460

Thr Thr Cys Ala Thr Thr Gly Cys Cys Gly Cys Ala Gly Cys Ala Ala
2465                2470                2475                2480

Gly Ala Thr Cys Ala Ala Gly Ala Thr Ala Cys Thr Ala Ala Gly
            2485                2490                2495

Gly Cys Ala Gly Ala Gly Ala Gly Gly Ala Gly Thr Thr Thr Ala Thr
            2500                2505                2510

Ala Thr Gly Cys Gly Gly Cys Thr Gly Ala Ala Ala Thr Thr Gly Ala
            2515                2520                2525

Thr Gly Ala Gly Ala Ala Gly Gly Thr Ala Ala Cys Ala Ala Thr Gly
            2530                2535                2540

Ala Ala Ala Ala Thr Cys Gly Gly Ala Thr Cys Ala Gly Ala Ala Cys
2545                2550                2555                2560

Ala Thr Thr Thr Thr Gly Ala Gly Cys Cys Ala Ala Gly Cys Gly Gly
            2565                2570                2575
```

-continued

```
Thr Cys Cys Cys Cys Ala Gly Ala Ala Cys Thr Gly Gly Ala Thr Thr
            2580                2585                2590

Gly Thr Thr Gly Cys Thr Gly Cys Thr Gly Ala Gly Gly Gly Thr Cys
        2595                2600                2605

Ala Ala Gly Ala Thr Thr Ala Cys Ala Ala Ala Ala Thr Cys Thr Gly
    2610                2615                2620

Gly Gly Ala Ala Gly Cys Gly Thr Cys Thr Thr Cys Ala Thr Ala Gly
2625                2630                2635                2640

Ala Cys Thr Thr Gly Gly Cys Gly Gly Gly Cys Thr Gly Cys Gly Ala
                2645                2650                2655

Gly Thr Gly Cys Cys Ala Thr Ala Thr Ala Ala Cys Thr Gly Cys Thr
            2660                2665                2670

Cys Ala Ala Ala Gly Ala Cys Thr Ala Ala Ala Ala Ala Gly Gly Ala
        2675                2680                2685

Ala Gly Cys Thr Ala Cys Ala Ala Gly Ala Ala Ala Gly Cys Ala Thr
    2690                2695                2700

Ala Ala Thr Gly Cys Thr Ala Gly Gly Ala Gly Ala Thr Gly Gly Cys
2705                2710                2715                2720

Gly Cys Cys Thr Cys Ala Gly Ala Ala Thr Gly Gly Thr Cys Ala Gly
                2725                2730                2735

Cys Thr Gly Gly Cys Gly Gly Gly Ala Gly Cys Thr Gly Cys Thr Gly
            2740                2745                2750

Cys Cys Gly Cys Thr Gly Cys Cys Gly Cys Cys Ala Thr Gly Gly Ala
        2755                2760                2765

Gly Cys Ala Gly Cys Ala Ala Ala Ala Thr Thr Cys Ala Ala Cys Ala
    2770                2775                2780

Ala Cys Ala Thr Ala Ala Gly Cys Thr Ala Thr Gly Gly Ala Ala Gly
2785                2790                2795                2800

Cys Ala Cys Thr Thr Gly Cys Cys Ala Cys Gly Gly Cys Gly Ala Thr
                2805                2810                2815

Ala Gly Gly Ala Thr Thr Ala Thr Cys Thr Ala Ala Thr Ala Gly Gly
            2820                2825                2830

Ala Cys Thr Ala Cys Thr Gly Thr Thr Gly Ala Ala Cys Ala Thr Thr
        2835                2840                2845

Cys Gly Ala Thr Ala Thr Ala Thr Cys Cys Ala Gly Ala Ala Cys Cys
    2850                2855                2860

Ala Cys Cys Cys Ala Thr Cys Ala Thr Thr Thr Gly Cys Ala Gly Gly
2865                2870                2875                2880

Cys Ala Cys Ala Thr Thr Gly Gly Cys Cys Ala Thr Thr Ala Ala Ala
                2885                2890                2895

Ala Thr Thr Thr Ala Gly Cys Thr Thr Cys Gly Thr Cys Cys Thr Cys
            2900                2905                2910

Thr Ala Thr Thr Thr Thr Gly Gly Ala Gly Cys Thr Ala Thr Gly Thr
        2915                2920                2925

Ala Ala Ala Ala Gly Cys Ala Thr Gly Cys Ala Cys Ala Ala Cys Thr
    2930                2935                2940

Cys Thr Ala Thr Thr Thr Ala Thr Gly Thr Gly Thr Gly Ala Ala Ala
2945                2950                2955                2960

Thr Ala Ala Ala Ala Thr Thr Thr Gly Ala Ala Ala Ala Cys Gly Cys
                2965                2970                2975

Gly Thr Gly Gly
            2980
```